US007352468B2

(12) United States Patent
Tarsa

(10) Patent No.: US 7,352,468 B2
(45) Date of Patent: Apr. 1, 2008

(54) CAVITY RING-DOWN DETECTION OF SURFACE PLASMON RESONANCE IN AN OPTICAL FIBER RESONATOR

(75) Inventor: Peter B. Tarsa, Duxbury, MA (US)

(73) Assignee: Trustees of Princeton University, Princeton, NJ (US)

( * ) Notice: Subject to any disclaimer, the term of this patent is extended or adjusted under 35 U.S.C. 154(b) by 404 days.

(21) Appl. No.: 11/021,572

(22) Filed: Dec. 23, 2004

(65) Prior Publication Data
US 2005/0117157 A1    Jun. 2, 2005

Related U.S. Application Data

(63) Continuation-in-part of application No. 10/644,137, filed on Aug. 20, 2003, now abandoned, which is a continuation-in-part of application No. 10/157,400, filed on May 29, 2002, which is a continuation-in-part of application No. 10/017,367, filed on Dec. 12, 2001, now Pat. No. 7,046,362.

(51) Int. Cl.
*G01N 21/55* (2006.01)
(52) U.S. Cl. .................................. 356/445; 250/227.14
(58) Field of Classification Search ........ 356/432–444, 356/445–448, 32; 250/227.14–227.16; 385/12
See application file for complete search history.

(56) References Cited

U.S. PATENT DOCUMENTS 1,719,443 A    7/1929   Nichterlein (Continued)

FOREIGN PATENT DOCUMENTS

DE    196 50 899 A1    6/1998

| DE | 19814575 A1 | 10/1999 |
|----|----|----|
| EP | 0 517 930 A1 | 12/1992 |
| EP | 1195582 A1 | 4/2002 |
| JP | 63013386 | 1/1988 |
| WO | WO 93/07469 | 4/1993 |

OTHER PUBLICATIONS

Lerber et al.; Cavity-ring down principle for fiber-optic resonators: experimental realization of bending loss and evanescent-field sensing; Applied Optics, OSA, Optical Society of America, Washington, DC, US, vol. 41, No. 18, Jun. 20, 2002, pp. 3567-3575.

(Continued)

*Primary Examiner*—Gregory J. Toatley, Jr.
*Assistant Examiner*—Tri Ton
(74) *Attorney, Agent, or Firm*—RatnerPrestia

(57) ABSTRACT

An apparatus and method for use with a coherent optical source to detect environmental changes. The apparatus comprises: an optical cavity, including an input coupling port, and an optical fiber section; a detector optically coupled to the optical cavity to monitor radiation in the optical cavity; and a processor electrically coupled to the detector for analyzing the environmental changes adjacent the detection portion of the optical cavity based on a rate of decay of the radiation in the optical cavity monitored by the detector. The optical fiber section of the optical cavity includes a detection portion coated with a conductive layer capable of supporting a surface plasmon to provide cavity loss. The surface plasmon is responsive to the environmental changes adjacent the detection portion. The coherent optical source is optically coupled to the input coupling port of the optical cavity to provide the radiation in the optical cavity.

74 Claims, 13 Drawing Sheets

U.S. PATENT DOCUMENTS

| | | | |
|---|---|---|---|
| 3,402,364 A | | 9/1968 | De Lang |
| 3,520,610 A | * | 7/1970 | Parrent, Jr. et al. ............ 356/71 |
| 3,711,788 A | | 1/1973 | Forkner |
| 3,976,368 A | | 8/1976 | McCann et al. |
| 3,982,203 A | | 9/1976 | De Wit |
| 4,161,436 A | | 7/1979 | Gould |
| 4,525,034 A | | 6/1985 | Simmons |
| 4,530,603 A | | 7/1985 | Shaw et al. |
| 4,578,793 A | | 3/1986 | Kane et al. |
| 4,677,639 A | | 6/1987 | Sasser |
| 4,740,986 A | | 4/1988 | Reeder |
| 4,746,201 A | | 5/1988 | Gould |
| 4,775,214 A | | 10/1988 | Johnson |
| 5,026,991 A | | 6/1991 | Goldstein et al. |
| 5,168,156 A | | 12/1992 | Fischer et al. |
| 5,276,548 A | | 1/1994 | Margalith |
| 5,463,493 A | | 10/1995 | Shah |
| 5,483,342 A | | 1/1996 | Rockwell |
| 5,528,040 A | | 6/1996 | Lehmann |
| 5,532,493 A | | 7/1996 | Hale et al. |
| 5,591,407 A | * | 1/1997 | Groger et al. ............ 422/82.05 |
| 5,835,231 A | | 11/1998 | Pipino |
| 5,912,740 A | | 6/1999 | Zare et al. |
| 5,973,864 A | | 10/1999 | Lehmann et al. |
| 5,986,768 A | | 11/1999 | Pipino |
| 6,097,555 A | | 8/2000 | Lehmann et al. |
| 6,172,823 B1 | | 1/2001 | Lehmann et al. |
| 6,172,824 B1 | | 1/2001 | Lehmann et al. |
| 6,466,322 B1 | | 10/2002 | Paldus et al. |
| 6,532,072 B1 | | 3/2003 | Largent |
| 6,795,190 B1 | * | 9/2004 | Paul et al. ................... 356/437 |
| 2003/0007715 A1 | | 1/2003 | Loock et al. |
| 2003/0109055 A1 | | 6/2003 | Lehmann et al. |
| 2004/0161804 A1 | | 8/2004 | McCash et al. |

OTHER PUBLICATIONS

International Search Report for PCT International Application No. PCT/US2005/046160 mailed Apr. 28, 2006.
J. White, Long Optical Paths of Large Aperture, 32 J. Opt. Soc. Amer., 285 (May 1942).
D. Heriott et al., Off-Axis Paths in Spherical Mirror Interferometers, 3 Appl. Opt. (4), 523 (Apr. 1964).
A. O'Keefe et al. Cavity Ring-Down Optical Spectrometer for Absorption Measurements Using Pulsed Laser Sources, 59 Rev, Sci. Instrum., 2544 (Dec. 1988).
D. Romanini et al., Ring-down Cavity Absorption Spectroscopy of the Very Weak HCN Overtone Bands with Six, Seven, and Eight Stretching Quanta, 99 J. Chem. Phys. (9), 6287-6301 (Nov. 1, 1993).
G. Rempe et al., Measurement of Ultralow Losses in an Optical Interferometer, 17 Opt. Letters (5), 363 (Mar. 1, 1992).
T. Yu et al., Kinetics of Pheynl Radical Reactions Studied by the "Cavity-Ring-Down" Method, 115 J. Am. Chem. Soc., 4371 (1993).
G. Meijer et al., Coherent Cavity Ring down Spectroscopy, 217 Chemical Physics Letters (1,2), 112 (Jan. 7, 1994).
J. Scherer et al., Cavity Ring Down Dye Laser Spectroscopy of Jet-Cooled Metal Clusters: $CU_2$ and $CU_3$, 172 Chemical Physics Letters (3,4), 214 (Sep. 7, 1990).
F. Stoelkel et al., Time Evolution of a Broadband Quasi-cw Dye Laser: Limitation of Sensitivity in Intracavity Laser Spectroscopy, 24 Applied Optics (21), 3591 (Nov. 1, 1985).
K. Lehmann et al., Molecules in the Stellar Environment, Experimental Measurements of Weak Bank Intensities in Molecules in the Stellar Environment, (Springer, 1994).
G. Gould et al., Crossed Roof Prism Interferometer, 1 Applied Optics (4), 533 (Jul. 1962).
A. Pipino et al., Evanescent Wave Cavity Ring-Down Spectroscopy with a Total-Internal Reflection Minicavity, 68 (8) Rev. Sci., Instrum., 2978 (Aug. 1997).
G. Stewart et al., An Investigation of an optical fibre amplifier loop for Intracavity and ring-down capacity loss measurements, Meas. Sci. Technol. 12: 843-849 (2001).
A. Dmitriev et al., Optical-fiber passive ring resonator in a low-mode radiation-propogration regime, J. Opt. Technol. 67:219-221 (2000).
S. Blair et al., Resonant-enhanced evanescent-wave fluorescence biosensing with cylindrical optical cavities, Applied Optics 0:570-582 (2001).
D. Littlejohn et al., Bent Silica Fiber Evanescent Absorption Sensors for Near-Infrared Spectroscopy, Applied Spectroscopy. 53: 845-849 (1999).
A. Messica et al., Theory of fiber-optic evanescent-wave spectroscopy and sensors, Applied Optics 35: 2274-2284 (1996).
Trautmann et al., Determination of the Deuterium Abundance in Water Using a CW Chemical DF Laser, Appl. Phys., 24: No. 1, 49-53 (1981).
S. Spammer et al., Interferometric distributed optical-fiber sensor, Applied Optics vol. 35, No. 22: 4522-4525 (Aug. 1996).
G. Boisde et al., Chemical and Biological Sensing with Optical Fibers and Waveguides, Boston, MA: Artech House (1996).
P. N. Moar et al., Fabrication, modeling and direct evanescent field measurement of tapered optical fiber sensors, J. Appl. Phys. 85: 3395-3398 (1999).
Y. Zaatar et al., Fabrication and characterization of an evanescent wave fiber optic sensor for air pollution control, Mat. Sci. Eng. B74: 296-298 (2000).
S. M. Lee et al., Evanescent-coupling Fiber Optic Pollution Monitoring System Using Etched D-Shape E-Core Fiber, Proc. SPIE-Int. Soc. Opt. Eng. 2836: 267-274, 1996.
J. Francisco et al., Optical Fiber Strain Gauge Based on a Tapered Singlel-Mode Fiber, pp. 90-96, Jul. 26, 1999, Sensors and Actuators 70 (2000).
P. M. Shankar et al., Coupling of modes in bent biconically tapered single-mode fibers, Journal of Lightwave Technology, 9 (7): 832-837 Jul. 1991.
K. Atherton et al., Fibre optic intra cavity spectroscopy-combined ring down and ICLAS architectures using fibre lasers, SPIE vol. 4204 (2001) pp. 124-130.
G. Stewart et al., Intra-Cavity and Ring-Down Cavity Absorption with Fibre Amplifiers for Trace Gas Detection, SPIE vol. 4185 (2000) pp. 448-451.
International Search Report dated May 16, 2003, application No. PCT/US 02/38421.
International Search Report dated May 20, 2003, application No. PCT/US 02/41689.

* cited by examiner

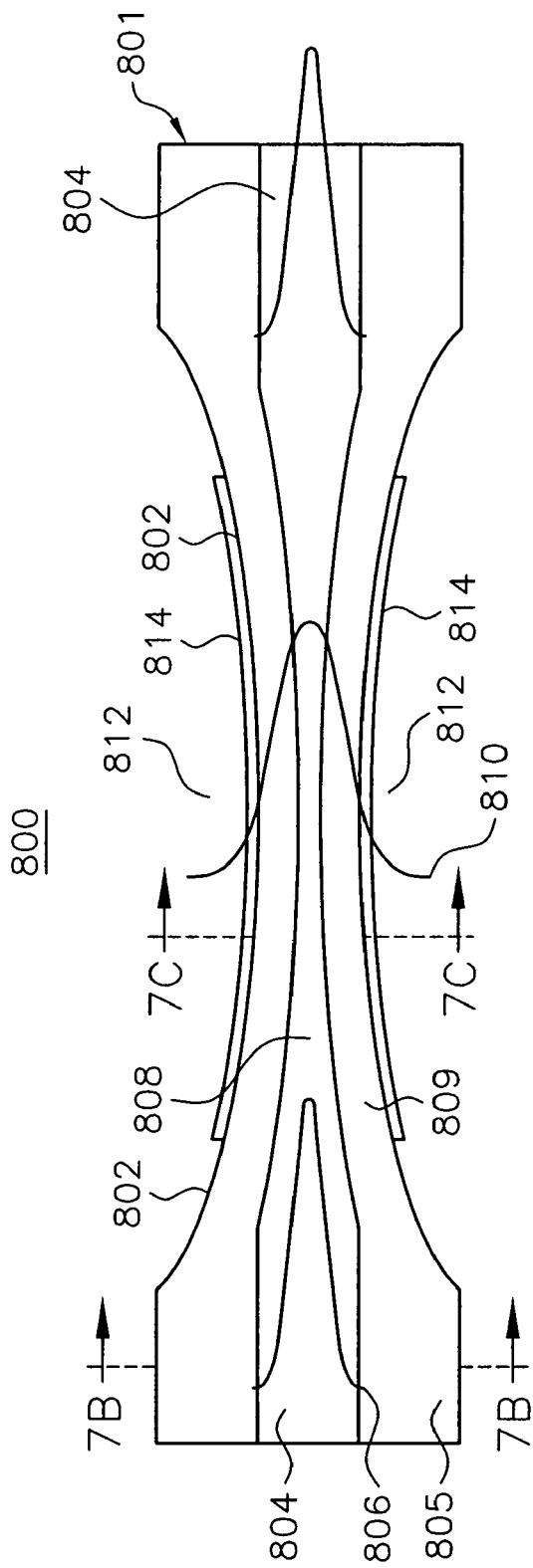
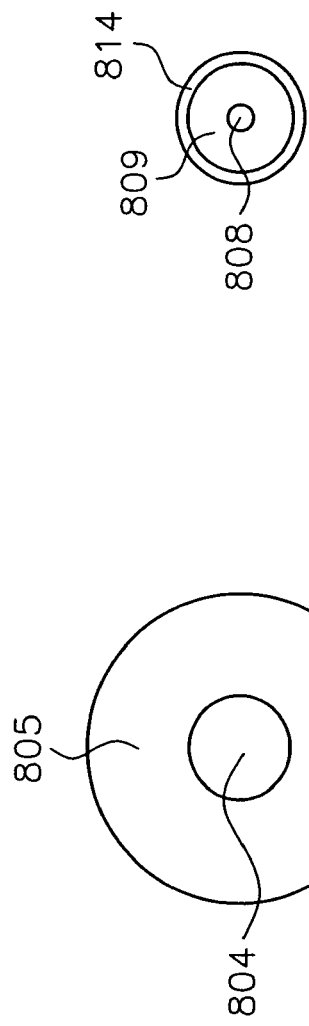
FIG. 7A
FIG. 7B
FIG. 7C

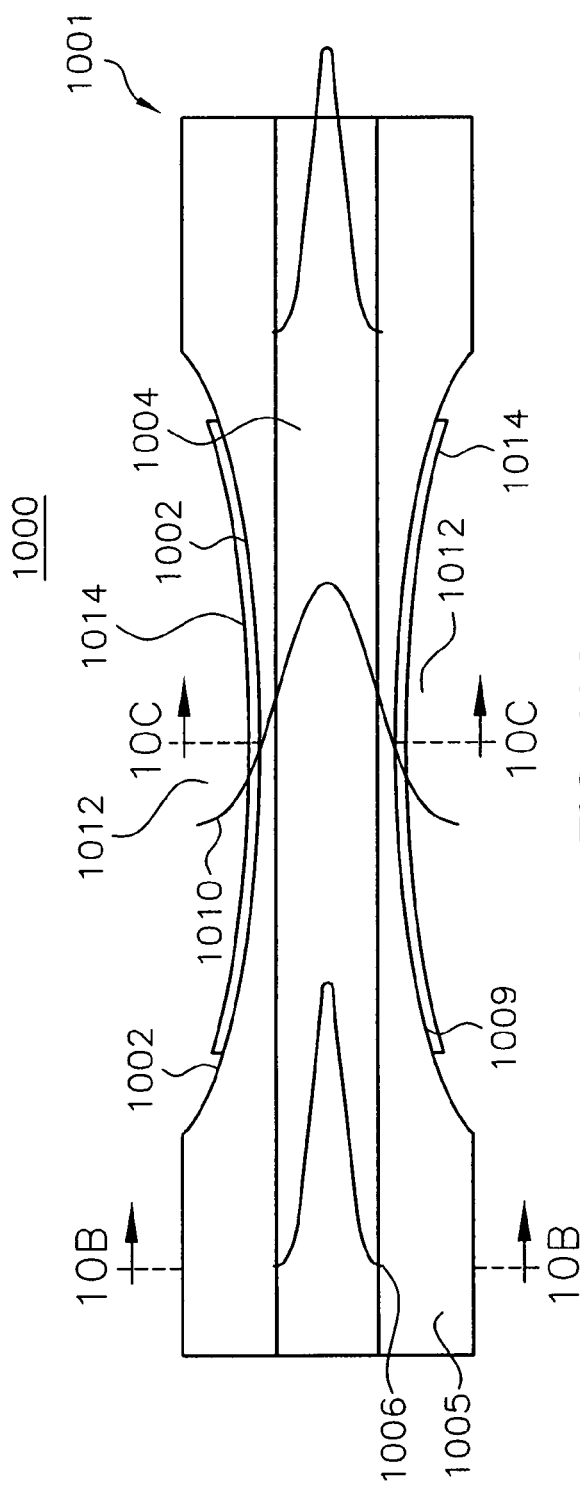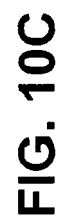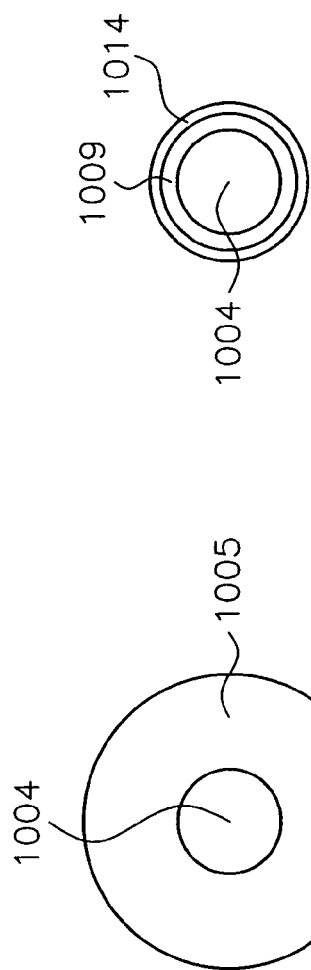
FIG. 10A
FIG. 10C
FIG. 10B

CAVITY RING-DOWN DETECTION OF SURFACE PLASMON RESONANCE IN AN OPTICAL FIBER RESONATOR

This application is a continuation-in-part of application Ser. No. 10/644,137 filed on Aug. 20, 2003 now abandoned, which is a continuation-in-part of pending application Ser. No. 10/157,400 filed on May 29, 2002, which is a Continuation-in-Part of application Ser. No. 10/017,367 filed on Dec. 12, 2001 now U.S. Pat. No. 7,046,362.

FIELD OF THE INVENTION

The present invention relates generally to cavity ring-down detection systems which include surface plasmon sensors and, in particular, is directed to measurement of environmental changes in the vicinity of the surface plasmon sensors using cavity ring-down spectroscopy. In particular the present invention may allow for highly sensitive detection of binding events at a coated fiber surface of the surface plasmon detectors.

BACKGROUND OF THE INVENTION

Although this application relates to measurement of environmental changes using cavity ring-down assisted surface plasmon detection, the following background in absorption spectroscopy may be useful in understanding the present invention.

Referring now to the drawing, wherein like reference numerals refer to like elements throughout, FIG. 1 illustrates the electromagnetic spectrum on a logarithmic scale. The science of spectroscopy studies spectra. In contrast with sciences concerned with other parts of the spectrum, visible optics particularly involves visible and near-visible light—a very narrow part of the available spectrum which extends in wavelength from about 1 mm to about 1 nm. Near visible light includes wavelengths slightly longer than red (infrared) and wavelengths slightly shorter than violet (ultraviolet). The range extends just far enough to either side of human visibility that the light can still be handled by most lenses and mirrors made of materials commonly used for visible optics. The wavelength dependence of optical properties of materials must often be considered to ensure that the optical elements formed of these materials have the desired effects.

Absorption-type spectroscopy offers high sensitivity, response times on the order of microseconds, immunity from poisoning, and limited interference from molecular species other than the species under study. Various molecular species may be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, it is desirable to measure and analyze the concentration of trace species in flowing gas streams and liquids with a high degree of speed and accuracy. Such measurement and analysis is required when the concentration of contaminants is critical to the quality of the end product, but may still be desirable even when not required. For example, gases such as $N_2$, $O_2$, $H_2$, Ar, and He are used to manufacture integrated circuits, for example, and the presence in those gases of impurities—even at parts per billion (ppb) levels—may prove damaging and reduce the yield of operational circuits. Therefore, the relatively high sensitivity with which water and other potential contaminants can be spectroscopically monitored is important to manufacturers of high-purity gases used in the semiconductor industry. These and various other impurities must be detected in many other industrial applications, as well.

Further, the presence of impurities, either inherent or deliberately released, in fluids of all kinds have become of particular concern recently. Spectroscopic methods provide a convenient means to monitor fluids such as gases and liquids (i.e. air and water) for contamination by hazardous chemical and biological agents. These methods may also be used for detection of chemical signatures of materials such as explosives and drugs.

In all of these applications, sensitivity is an important concern for any detection method. Spectroscopy has obtained parts per million (ppm) level detection for gaseous contaminants in high-purity gases. Detection sensitivities at the ppb level are attainable in some cases. Accordingly, several spectroscopic methods have been applied to such applications as quantitative contamination monitoring in gases, including: absorption measurements in traditional long path length cells, photoacoustic spectroscopy, frequency modulation spectroscopy, and intracavity laser absorption spectroscopy. Unfortunately, these methods have several features, discussed in U.S. Pat. No. 5,528,040 issued to Lehmann, that have made them difficult to use and impractical for industrial applications. They have been largely confined, therefore, to laboratory investigations.

In contrast, cavity ring-down spectroscopy (CRDS) has become an important spectroscopic technique with applications to science, industrial process control, and atmospheric trace gas detection. CRDS has been demonstrated as a technique for the measurement of optical absorption that excels in the low-absorbance regime where conventional methods have inadequate sensitivity. CRDS utilizes the mean lifetime of photons in a high-finesse optical resonator as the absorption-sensitive observable.

Typically, the resonator includes a pair of nominally equivalent, narrow band, ultra-high reflectivity dielectric mirrors, configured appropriately to form a stable standing wave optical cavity, or resonator. A laser pulse is injected into the resonator through one of the mirrors to experience a mean lifetime which depends upon the photon round-trip transit time, the length of the resonator, the absorption cross section and number density of the species being detected, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CRDS is determined by the magnitude of the intrinsic resonator losses, which can be minimized with techniques such as superpolishing that permit the fabrication of ultra-low-loss optics.

At present, CRDS is limited to spectroscopic regions where high reflectivity dielectric mirrors are produced. This has significantly limited the usefulness of the method in much of the ultraviolet and infrared regions, because mirrors with sufficiently high reflectivity are not presently available. Even in regions where suitable dielectric mirrors are available, each set of mirrors only allows for operation over a small range of wavelengths, typically a fractional range of a few percent. Further, construction of many dielectric mirrors requires use of materials that may degrade over time, especially when exposed to chemically corrosive environments. Because these present limitations restrict or prevent the use of CRDS in many potential applications, there is a clearly recognized need to improve upon the current state of the art with respect to resonator construction.

When light impinges on a surface of lower index of refraction that the propagation medium at greater than a critical angle, it reflects completely, i.e. it exhibits total internal reflection (TIR). J. D. Jackson, "Classical Electrodynamics," Chapter 7, John Wiley & Sons, Inc.: New York, N.Y. (1962). A field exists, however, beyond the point of reflection that is non-propagating and decays exponentially with distance from the interface. This evanescent field carries no power in a pure dielectric medium, but attenuation of the reflected wave allows observation of the presence of an absorbing species in the region of the evanescent field. F. M. Mirabella (ed.), "Internal Reflection Spectroscopy," Chapter 2, Marcel Dekker, Inc.: New York, N.Y. (1993). The article by A. Pipino et al., "Evanescent wave cavity ringdown spectroscopy with a total-internal reflection minicavity," Rev. Sci. Instrum. 68 (8) (August 1997), presents an approach to improved resonator construction using TIR. This approach uses a monolithic, TIR ring resonator (i.e. a traveling wave optical cavity) of regular polygonal geometry (e.g., square and octagonal) with at least one convex facet to induce stability. A light pulse is totally reflected by a first prism located outside and in the vicinity of the resonator, creating an evanescent wave which enters the resonator and excites the stable modes of the resonator through photon tunneling.

The absorption spectrum of matter located at the totally reflecting surfaces of this resonator is obtained from the mean lifetime of a photon in the monolithic resonator, which is extracted from the time dependence of the signal received at a detector by out coupling with a second prism (also a totally reflecting prism located outside, but in the vicinity of, the resonator). Thus, optical radiation enters and exits the resonator by photon tunneling, which permits precise control of input and output coupling. A miniature-resonator realization of CRDS results and the TIR-ring resonator extends the CRDS concept to condensed matter spectroscopy. The broadband nature of TIR circumvents the narrow bandwidth restriction imposed by dielectric mirrors in conventional gas-phase CRDS. It is noted that the work of A. Pipino et al. is only applicable to TIR spectroscopy, which is intrinsically limited to short overall absorption path lengths, and thus powerful absorption strengths.

Various novel approaches to mirror based CRDS systems are provided in U.S. Pat. Nos. 5,973,864; 6,097,555; 6,172, 823 B1; and 6,172,824 B1 issued to Lehmann et al., and incorporated herein by reference. These approaches teach the use of a near-confocal resonator formed by two reflecting elements or prismatic elements.

FIG. 2 illustrates prior art CRDS detector 10 in which ring down cavity (RDC) cell 60 is shown a standing wave configuration. As shown in FIG. 2, light is generated by narrow band, tunable, continuous wave diode laser 20. Laser 20 may be temperature tuned by a temperature controller 30 to adjust its wavelength to the desired spectral line of the analyte. An isolator 40 is positioned in front of and in line with the radiation emitted from laser 20. Isolator 40 provides a one-way transmission path, allowing radiation to travel away from laser 20 while preventing radiation from traveling in the opposite direction. Such an isolator desirably reduces noise in laser 20 caused by unwanted reflection or scattering of light back into the laser cavity. Single mode fiber coupler (F.C.) 50 couples the light emitted from laser 20 into the optical fiber 48. Fiber coupler 50 is positioned in front of and in line with isolator 40. Fiber coupler 50 receives and holds optical fiber 48 and directs the radiation emitted from laser 20 toward and through a first lens 46. First lens 46 collects and focuses the radiation. Because the beam pattern emitted by laser 20 does not perfectly match the pattern of light propagating in optical fiber 48, there is an inevitable mismatch loss. It is noted that free space optics may be used alternatively to transmit the laser light.

The laser radiation is approximately mode-matched into RDC cell 60. A reflective mirror 52 directs the radiation toward a beam splitter 54. Beam splitter 54 directs about 90%, of the radiation through a second lens 56. Second lens 56 collects and focuses the radiation into cell 60. The remaining radiation passes through beam splitter 54 and is directed by a reflective mirror 58 into an analyte reference cell 90.

The radiation which is transmitted through analyte reference cell 90 is directed toward and through a fourth lens 92. Fourth lens 92 is aligned between analyte reference cell 90 and a second photodetector 94 (PD 2). Photodetector 94 provides input to computer and control electronics 100.

Cell 60 is made from two, highly reflective mirrors 62, 64, which are aligned as a near confocal etalon along an axis, a. Mirrors 62, 64 constitute the input and output windows of cell 60. The sample gas under study flows through a narrow tube 66 that is coaxial with the optical axis, a, of cell 60. Mirrors 62, 64 are placed on adjustable flanges or mounts that are sealed with vacuum tight bellows to allow adjustment of the optical alignment of cell 60.

Mirrors 62, 64 have a high-reflectivity dielectric coating and are oriented with the coating facing inside the cavity formed by cell 60. A small fraction of laser light enters cell 60 through front mirror 62 and "rings" back and forth inside the cavity of cell 60. Light transmitted through rear mirror 64 (the reflector) of cell 60 is directed toward and through a third lens 68 and, in turn, imaged onto a first photodetector 70 (PD 1). Each of photodetectors 70, 94 converts an incoming optical beam into an electrical current and, therefore, provides an input signal to computer and control electronics 100. The input signal represents the decay rate of the cavity ring down.

FIG. 3 illustrates optical path within prior art prism based CRDS resonator 100 which is designed to operate in a traveling wave configuration. As shown in FIG. 3, resonator 100 for CRDS is based upon using two Brewster's angle retroreflector prisms 150 and 152. The polarizing or Brewster's angle, $\Theta_B$, is shown relative to prism 150. Incident light 12 and exiting light 14 are illustrated as input to and output from prism 152, respectively. The resonant optical beam undergoes two total internal reflections without loss in each prism 150 and 152 at about 45°, an angle which is greater than the critical angle for fused quartz and most other common optical prism materials within the visible spectrum. Light travels between prisms 150 and 152 along optical axis 154. Alternatively, three or more high reflectivity mirrors may be used to form mirror based traveling wave RDC. A traveling wave RDC, such as prism based CRDS resonator 100, may be used in the place of standing wave RDC 60 in CRDS detector 10 shown in FIG. 2.

In both of the traveling wave RDC's described precise alignment of the prisms, or mirrors, with each other and with the input and output beams is necessary. Precise tuning of the distance between mirrors 62 and 64 may also be desirable in standing wave RDC 60 to allow the laser light to resonate within the optical cavity. This means that these cavities may be adversely affected by environmental changes such as changes in temperature or refractive index of the medium in the cavity.

As described by the inventors in pending application Ser. No. 10/644,137 filed on Aug. 20, 2003, and its predecessors Ser. No. 10/157,400 filed on May 29, 2002, and Ser. No. 10/017,367 filed on Dec. 12, 2001, from which the present application proceeds, the use of a passive fiber optic ring resonator in a CRDS detector may prove useful in overcoming at least some of the difficulties of using prior art RDC's such as those illustrated in FIGS. 2 and 3. The present invention utilizes surface plasmon resonance to improve the sensitivity of CRDS detectors.

SUMMARY OF THE INVENTION

An exemplary embodiment of the present invention is a fiber-based surface plasmon resonance (SPR) detector formed in an optical fiber section, including a tapered fiber portion of the optical fiber section having an outer surface and a conductive layer capable of supporting a surface plasmon formed on the outer surface of the tapered fiber portion. This surface plasmon formed on the outer surface of the tapered fiber portion is responsive to environmental changes adjacent the tapered fiber portion.

Another exemplary embodiment of the present invention is an apparatus for use with a coherent optical source to detect environmental changes, including: an optical cavity, including an input coupling port, and an optical fiber section; a detector optically coupled to the optical cavity to monitor radiation in the optical cavity; and a processor electrically coupled to the detector for analyzing the environmental changes adjacent the detection portion of the optical cavity based on a rate of decay of the radiation in the optical cavity monitored by the detector. The optical fiber section of the optical cavity includes a detection portion coated with a conductive layer capable of supporting a surface plasmon to provide cavity loss. The surface plasmon is responsive to the environmental changes adjacent the detection portion. The coherent optical source is optically coupled to the input coupling port of the optical cavity to provide the radiation in the optical cavity.

An additional exemplary embodiment of the present invention is an apparatus to detect binding events for use with a coherent source that emits radiation, including: a passive, closed fiber optic ring; a sensor having a predetermined shape, a conductive coating, and being in line with the passive, closed fiber optic ring; coupling means for i) optically coupling at least a portion of the radiation emitted by the coherent source into the fiber optic ring to generate the propagating field and ii) transmitting a detection portion of the propagating field; a detector for detecting a power level of the detection portion of the propagating field transmitted by the coupling means; a processor electrically coupled to the detector for determining the level of the binding events on the surface of the conductive coating of the sensor. The conductive coating of the sensor is capable of supporting a surface plasmon driven by a propagating field in the passive, closed fiber optic ring and is responsive to a level of the binding events at a surface of the conductive coating. The detector generates a signal responsive to the detected power level of the detection portion of the propagating field and the processor determines the level of the binding events based on a rate of decay of the power level of the detection portion of the propagating field detected by the detector.

A further exemplary embodiment of the present invention is an improved method of detecting environmental changes in a fluid using a surface plasmon cavity ring-down detection (SPCRD) system that includes a surface plasmon resonance (SPR) sensor optically coupled within an optical cavity. The SPR sensor is formed of a metal-coated tapered optical fiber section. Coherent optical radiation, including a predetermined wavelength, is coupled into the optical cavity of the SPCRD system. The power level of the coherent optical radiation in the optical cavity is monitored and a baseline cavity loss of the optical cavity is determined based on the monitored power level. The SPR sensor is exposed to the fluid and a detection cavity loss of the optical cavity is determined based on the new monitored power level following exposure of the SPR sensor to the fluid. Environmental changes in the fluid are detected based on differences between the baseline cavity loss and the detection cavity loss of the optical cavity.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 7A, 9A, and 10A are side cut-away drawings illustrating exemplary surface plasmon resonance (SPR) sensors according to an exemplary embodiment of the present invention.

FIGS. 7B and 7C are end cut-away drawings illustrating features of the exemplary SPR sensor illustrated in FIG. 7A.

FIGS. 10B and 10C are end cut-away drawings illustrating features of the exemplary SPR sensor illustrated in FIG. 10A.

DETAILED DESCRIPTION OF THE INVENTION

Figure 1:
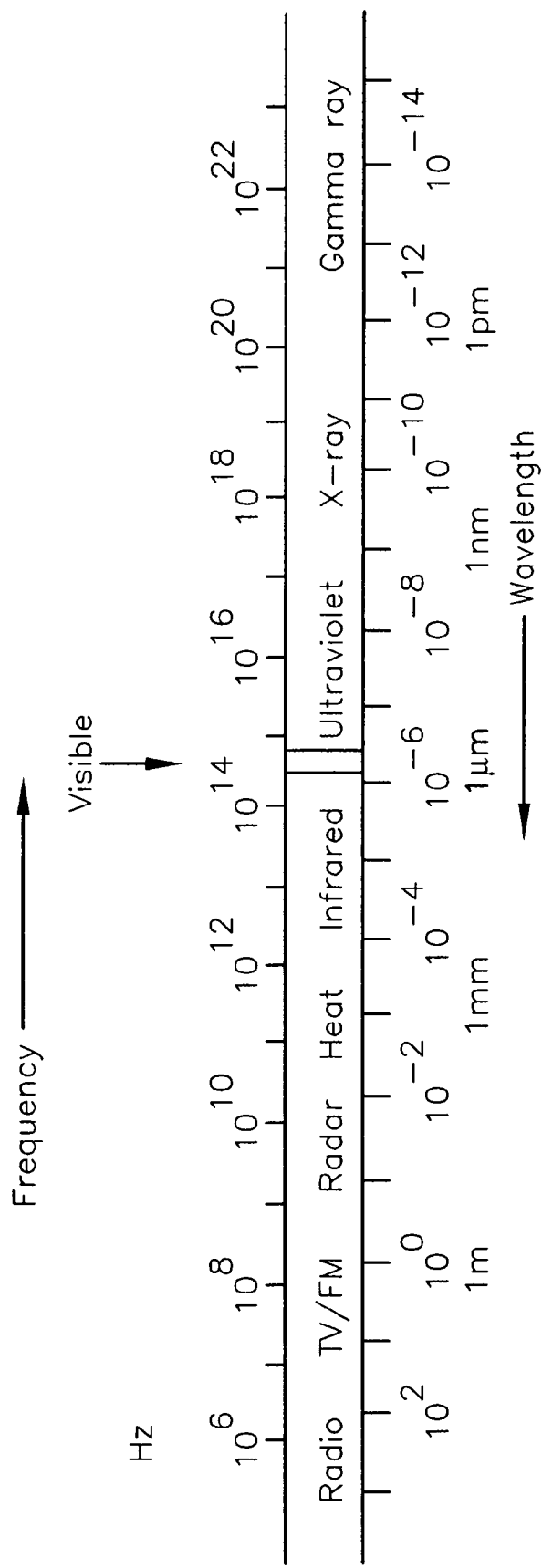
FIG. 1 is a graph illustrating the electromagnetic spectrum on a logarithmic scale.

The entire disclosure of U.S. patent application Ser. No. 10/644,137 filed on Aug. 20, 2003; Ser. No. 10/157,400 filed on May 29, 2002; and Ser. No. 10/017,367 filed Dec. 12, 2001 are expressly incorporated herein by reference.

As described above, CRDS provides a highly sensitive means of measuring analytes in a medium within an optical cavity. Further, Applicants have described in Ser. No. 10/157,400 filed on May 29, 2002 and Ser. No. 10/017,367 filed Dec. 12, 2001 methods of using the evanescent fields surrounding optical fibers to provide loss in exemplary optical fiber-based ring-down cavities. The present invention extends these methods through the use of surface plasmon resonance (SPR) techniques to improve sensor sensitivity and to expand the types of environmental changes that may be sensed with exemplary sensors according to the present invention.

SPR spectroscopy is used to measure small changes in refractive index on an external surface of a total internal reflection (TIR) element that has been coated with a conductive coating. Surface plasmons may be generated along the surface of thin conductive coatings formed on a TIR surface, if the light has a resonant wavelength that corresponds to its angle of incidence. The resonant wavelength for a given angle of incidence is dependent on the difference in refractive index between the substrate of the TIR element and the external medium adjacent the conductive coating. The range of wavelength, or angle of incidence, of the light for which there is significant generation of surface plasmons is typically very small, allowing SPR spectroscopy to provide a very sensitive means of measuring changes in refractive index. SPR-based sensors may either directly detect the surface plasmons, or they may detected energy lost from the incident light beam by conversion into the surface plasmons.

SPR detection systems commonly use prisms as the TIR element, but SPR techniques have been extended incorporate tapered optical fiber sensors as TIR elements. These sensors include a tapered optical fiber with a continuous range of angles along the taper transition, thus requiring variation only of the wavelength of light being used for signal resolution. The light is coupled to form a single pass, multi-angle SPR detection system. Resolution of such a system may be dependent on the rate of change of the angle of incidence in the tapered portion of the fiber.

By accumulating the loss over a large number of passes, CRDS provides a highly sensitive method for detection of loss in an optical element. Pipino et al., discussed above, first demonstrated the feasibility of incorporating these two techniques, SPR and CRDS, by using a monolithic, TIR ring resonator. This system may provide high sensitivity detection, but the alignment requirements for coupling light in and out of the monolithic, TIR ring resonator used reduces the utility of this system for most practical applications, where flexibility and mobility are desired.

By incorporating a coated fiber taper SPR sensor within an optical resonator, the present invention allows benefits of both SPR and CRDS to be realized in a more practical system. For example, refractive index measurements using a conductively coated fiber taper SPR sensing region incorporated in a fiber ring resonator may benefit from the improved sensitivity of CRDS. The portion of the fiber ring including the conductively coated fiber taper SPR sensing region may be easily manipulated to sense the refractive index of various fluid media, such as dipping it into a flow of liquid, gas, or a suspension. The use of CRDS may also be exploited to help resolve noisy SPR signals and improve sensitivity to environmental changes adjacent the surface.

Figure 4:
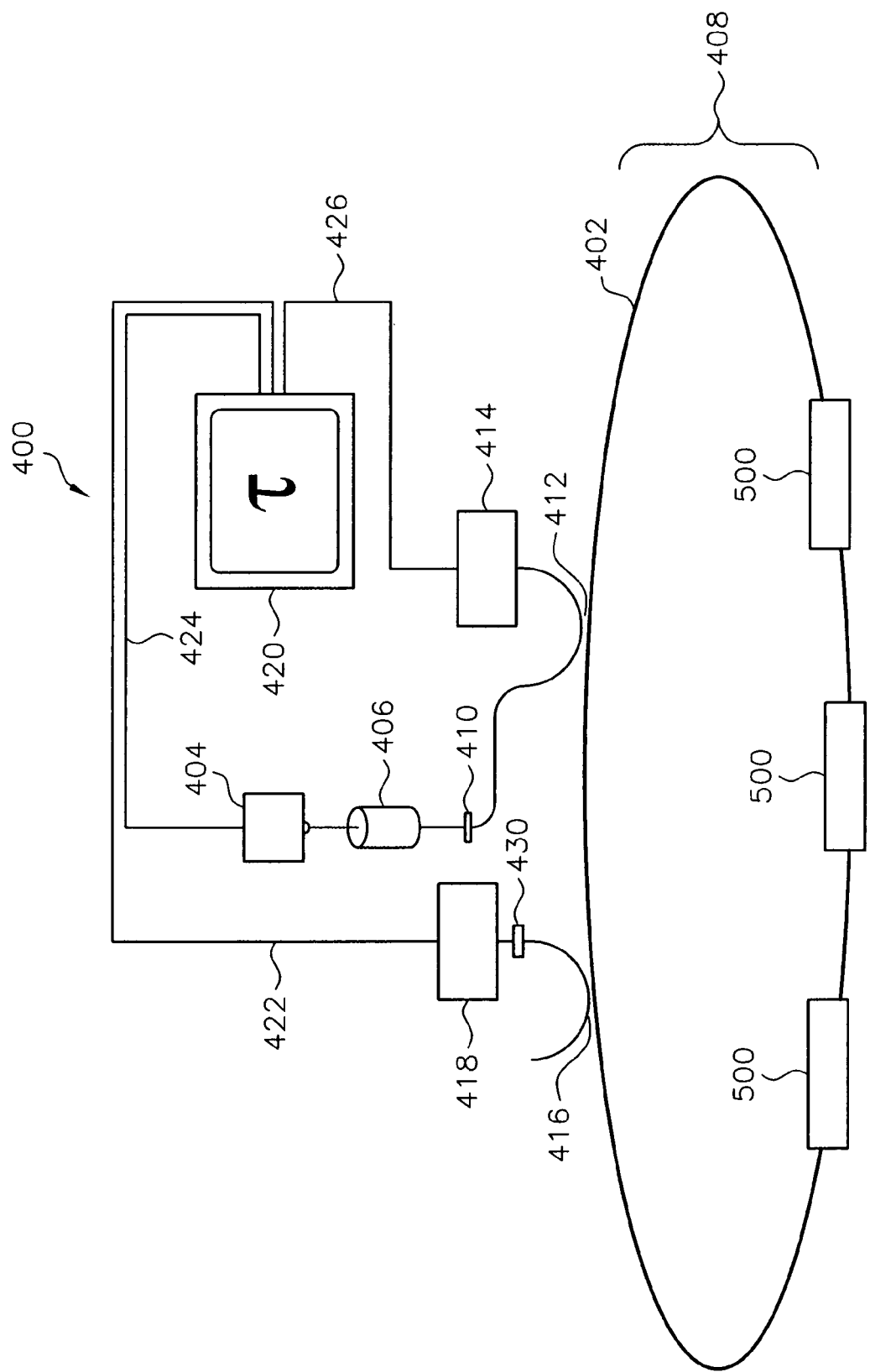
FIG. 4 is a schematic block diagram illustrating an exemplary surface plasmon cavity ring-down detection (SPCRD) system according to an exemplary embodiment of the present invention.

FIG. 4 illustrates fiber optic based ring-down apparatus 400 with SPR sensors 500 according to an exemplary embodiment of the present invention. This exemplary apparatus may detect environmental changes in fluids surrounding SPR sensors 500, including detecting a change in the chemical composition of the adjacent fluid including detecting the presence of trace species, or analytes, in gases and liquids. Other possible environmental changes that may be detected by SPR sensors 500 include changes in: the index of refraction of media adjacent the detection portion of the sensor; the ambient temperature adjacent the detection portion of the sensor; and the electric field adjacent the detection portion of the sensor, as well as the presence of ionizing radiation adjacent the sensor.

In FIG. 4, apparatus 400 includes resonant fiber optic ring 408 which has fiber optic cable 402 and SPR sensors 500 (described below in detail) distributed along the length of fiber optic cable 402. Although other optical cavities may be used in alternative embodiments of the present invention, an exemplary closed optical fiber ring cavity, such as resonant fiber optic ring 408 shown in FIG. 4, may desirably have lower cavity losses, other than the environmentally dependent losses provided by SPR sensors 500. Lower cavity losses may allow for detection of smaller environmentally dependent losses, which leads to greater system sensitivity for detection of environmental changes.

The length of resonant fiber optic ring 408 is easily adaptable to a variety of acquisition situations, such as perimeter sensing or passing through various sections of a physical plant, for example. It is contemplated that the length of the optical cavity in an exemplary apparatus of the present invention may be as small as about 1 meter or as large as several kilometers. Although as shown, three SPR sensors 500 are distributed along the length of fiber optic loop 408, the invention may be practiced using only one SPR sensor 500, if desired. The distribution of more than one SPR sensor 500 may allow for sampling of an environmental change at various points throughout the installation site. Alternatively, each of the several SPR sensors may be designed to respond to different environmental changes, and/or different analytes.

Figure 3:
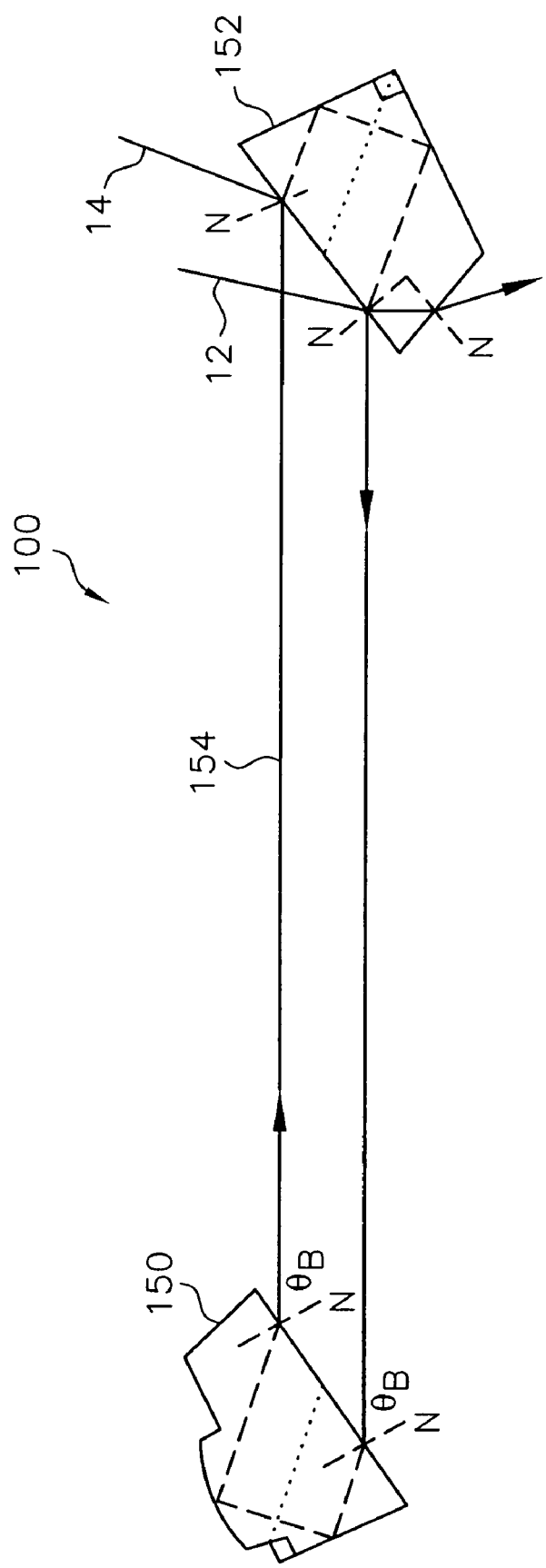
FIG. 3 is a top plan drawing illustrating a prior art traveling wave CRDS cell using prisms.

Although the exemplary system shown in FIG. 4 utilizes a complete optical fiber ring cavity, it is noted that the optical cavity of an exemplary surface plasmon cavity ring-down detection (SPCRD) system according to the present invention may also be formed with a combination of optical fiber and free space optics forming the optical cavity. For example, a section of optical fiber, including at least one SPR sensor, may be introduced along one of the arms of beam path 154 in the exemplary optical cavity of FIG. 3. One potential advantage of this alternative embodiment is the ability to easily exchange optical fiber sections that include different SPR sensors in this exemplary SPCRD system, allowing the SPCRD system to sense any of a number of different environmental changes as desired.

Additionally, it is noted that a standing wave optical cavity may be used in an exemplary SPCRD system as well.

Figure 2:
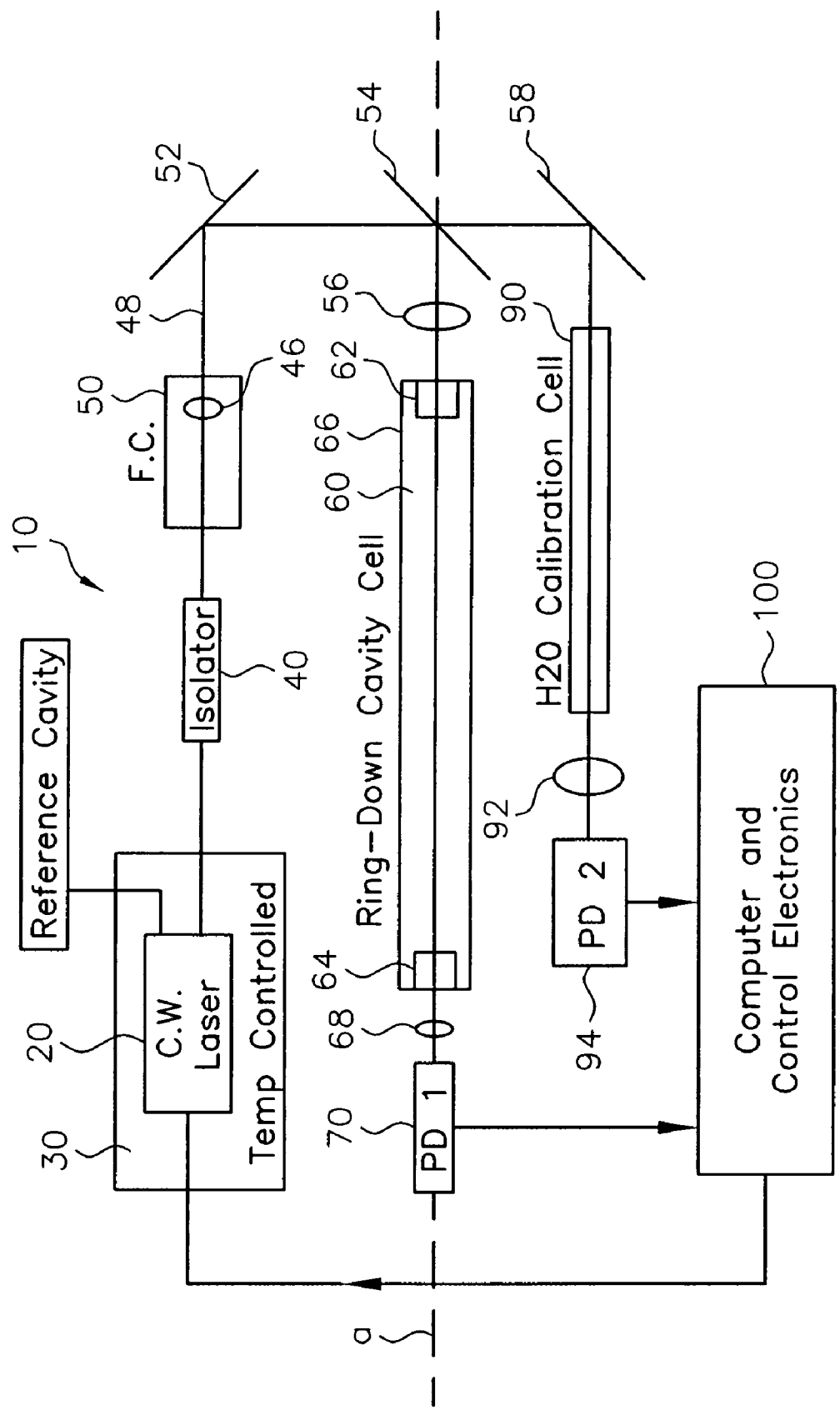
FIG. 2 is a schematic block diagram illustrating a prior art standing wave CRDS system using mirrors.
Figure 11:
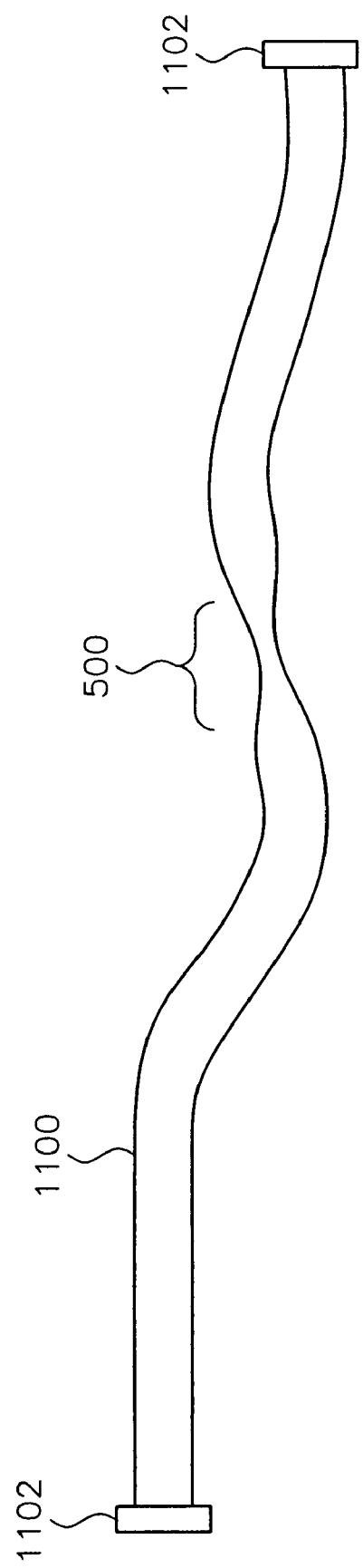
FIG. 11 is a top plan drawing illustrating an exemplary fiber based traveling wave CRDS cell for SPCRD according to an exemplary embodiment of the present invention.

FIG. 11 illustrates exemplary optical fiber standing wave cavity 1100, which includes reflectors 1102 that also serve as input and output couplers. This optical cavity is similar to RDC 60 in FIG. 2, except that, because it is formed of a section of optical fiber, exemplary optical fiber standing wave cavity 1100 is flexible, allowing greater freedom and versatility for a SPCRD system incorporating such an optical cavity. It is noted that reflectors 1102 may be dielectric or metal mirrors formed directly on the cleaved ends of optical fiber standing wave cavity 1100, or, alternatively, they may be optically coupled to optical fiber standing wave cavity 1100 by free space optics (not shown). It is noted that in this alternative embodiment it is desirable to locate SPR detector 500 along the length of optical fiber standing wave cavity 1100 such that at least one antinode of the standing wave pattern formed within the cavity is located in the SPR sensor. If the sensitive portion of the SPR sensor is one or more wavelengths long, this condition may be easily met.

Coherent source of radiation 404, which may be an optical parametric generator (OPG), optical parametric amplifier (OPA), a laser, or other coherent source, desirably emits radiation at a wavelength consistent with a surface plasmon resonance wavelength of SPR sensor(s) 500. Coherent source 404 may be a tunable diode laser having a narrow band. Alternatively, coherent source 404 may include more than one optical source to provide radiation at several wavelengths. These wavelengths may correspond to different ones of SPR sensors 500 or they may correspond to surface plasmon resonances for different environmental changes and/or different analytes. An example of a commercially available optical parametric amplifier is model no. OPA-800C available from Spectra Physics, of Mountain View, Calif.

It is contemplated that the present invention may be used to detect a variety of chemical and biological agents harmful to humans and/or animals in a fluid. The presence of such chemical and biological agents may cause a sufficient change in the index of refraction of the fluid that they may be detected SPR sensors 500. It is also contemplated that such detection may be enhanced by coating the outer surface of SPR layer 814 (located on tapered optical fiber section 802) with antibodies that specifically bind the desired agent as shown in FIGS. 7A and 8A. These antibodies may be deposited on conductive layer 816 to form functionalized chemical coating 818, which changes its refractive index in response number of agents bond by the antibodies. It is noted that functionalized chemical coating 818 may alternatively be formed of materials which change their refractive index in response to other specific environmental parameters, such as temperature, humidity, pH, electric field, ionizing radiation, etc.

In the exemplary embodiment SPCRD system of FIG. 4, radiation from coherent source 404 is desirably provided to resonant fiber optic ring 408 through optional optical isolator 406, coupler 410, and evanescent input coupler 412. Alternatively, an optical grating-base coupler may be used instead of evanescent input coupler 412. In SPCRD systems that utilize free space optics in a traveling wave cavity or include a standing wave cavity, radiation may be coupled into the cavity through a high reflectivity mirror or TIR prism surface of the optical cavity as well. When coherent source 404 is a diode laser, using optical isolator 406 help minimize noise in the laser by preventing reflections back into the laser. Evanescent input coupler 412 may provide a fixed percentage of radiation from coherent source 404 into resonant fiber optic ring 408, or may be adjustable based on losses present throughout resonant fiber optic ring 408. Preferably, the amount of radiation provided by evanescent input coupler 412 (or other couplers) to resonant fiber optic ring 408 matches the losses present in fiber optic cable 402 and the connectors (not shown) of the optical cavity, allowing a steady state of radiation resonating in the cavity. A commercially available evanescent coupler providing 1% coupling (99%/1% split ratio coupling) of radiation is manufactured by ThorLabs of Newton, N.J., having part number 10202A-99. In a preferred embodiment, evanescent input coupler 412 couples less that 1% of the radiation from coherent source 404 into fiber 402.

Figure 5:
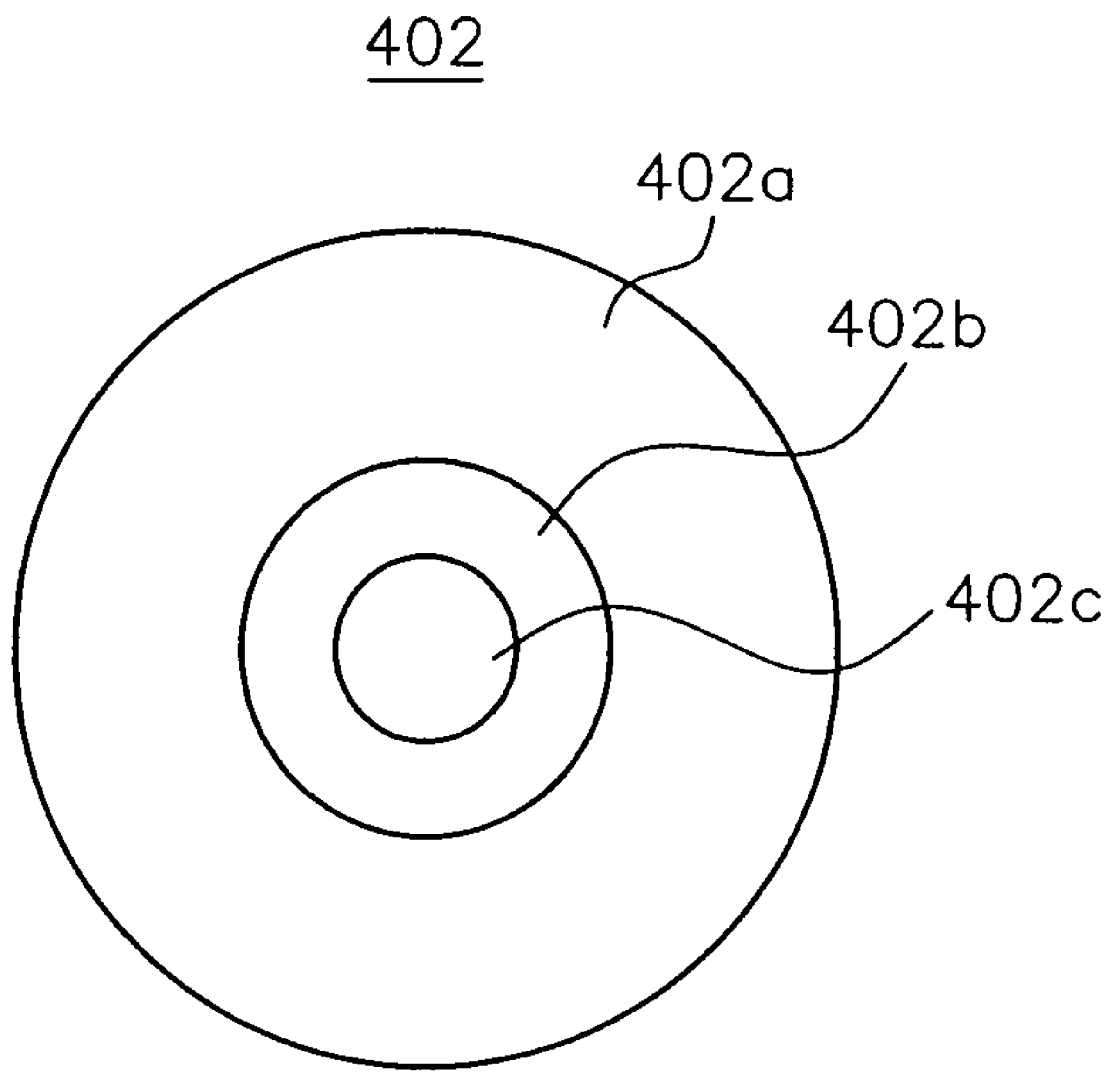
FIG. 5 is an end plan drawing illustrating a conventional optical fiber.

A cross section of fiber optic cable 402 is shown in FIG. 5. To form SPR sensors 500, a portion of the jacket 402a covering fiber optic cable 402 is removed to expose cladding 402b that surrounds inner core 402c of fiber optic cable 402. Alternatively, both jacket 402a and cladding 402b may be removed to expose inner core 402c. However, this alternative may not be most desired because of the brittle nature of inner core 402c used in certain types of fiber optic cables.

It is contemplated that the removal of jacket 402a (in any of the exemplary SPR sensors shown in the drawing) may be accomplished by mechanical means, such as a conventional fiber optic stripping tool, or by immersing the portion of the fiber cable in a solvent that will attack and dissolve jacket 402a without effecting cladding 402b and inner core 402c. In the case of partial removal of jacket 402a, the solvent approach may be modified by selectively applying the solvent to the portion of the jacket intended for removal.

Figure 6:
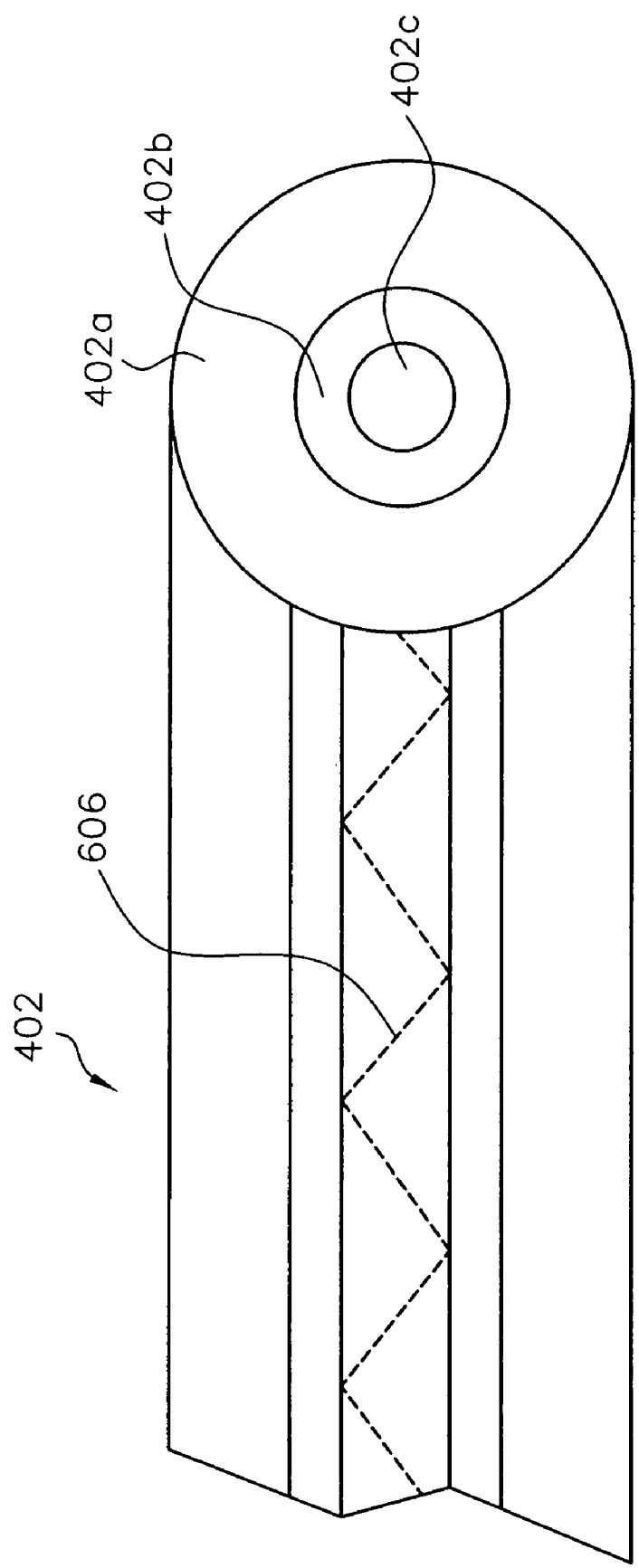
FIG. 6 is a perspective drawing illustrating a conventional optical fiber.

FIG. 6 provides an exemplary illustration of how radiation propagates through fiber optic cable 402. As shown in FIG. 6, radiation 606 exhibits total internal reflection (TIR) at the boundary between inner core 402c and cladding 402b. There is some negligible loss (not shown) by which radiation is not reflected, but is absorbed into cladding 402b. Although FIG. 6 is described as a fiber optic cable, FIG. 6 and the exemplary embodiments of the present inventions are equally applicable to a hollow fiber, such as a hollow waveguide, in which cladding 402b surrounds a hollow core.

Referring again to FIG. 4, the radiation that remains after passing through sensors 500 continues through fiber loop 402. A portion of that remaining radiation is coupled out of fiber optic loop 402 by evanescent output coupler 416. Evanescent output coupler 416 is coupled to processor 420 through detector 418 and signal line 422. Detector 418 may be any typical analog photodetector such as a photodiode, a photoresistor, or a phototransistor.

It is noted that radiation from coherent source 404 may alternatively be coupled into and out of resonant fiber optic ring 408 through a single evanescent input/output coupler. This evanescent input/output coupler may provide a fixed percentage of radiation from coherent source 404 into resonant fiber optic ring 408, or may be adjustable based on losses present throughout resonant fiber optic ring 404. In this alternative exemplary embodiment the evanescent input/output coupler is essentially a reconfiguration of evanescent input coupler 412 and output coupler 416 discussed above with respect to the exemplary embodiment of FIG. 4. Desirably, this evanescent input/output coupler couples less that 1% of the radiation from laser 404 into fiber 402. Wavelength selector 430 may also be controlled by processor 420 to prevent radiation from coherent source 404 "blinding" detector 418 during the time period after the radiation from coherent source 404 was coupled into fiber 402. In a further alternative embodiment, detector 418 may be replaced by an in-line electroabsorption detector (not shown), making an output coupler unnecessary. Desirably, this electroabsorption detector absorbs less that 1% of the radiation from laser 404 during detection.

Processor 420 may be a personal computer, for example, having a means for converting the analog output of detector 418 into a digital signal for processing and being programmed to perform analysis of this digital signal. Alternatively, another processor means such as a digital signal processor, special purpose circuitry, or an ASIC may be used as processor 420. Processor 420 also desirably controls coherent source 404 through control line 424. Once the signals are received from detector 418 by processor 420, the processor may determine the amount and type of environment change measured based the amount of loss due to surface plasmons detected. This loss may be determined based on the decay rate of radiation in the cavity for pulsed coherent sources, or the steady state energy level of radiation in the cavity for CW coherent sources.

Optionally, wavelength selector 430 may be placed between evanescent output coupler 416 and detector 418. Wavelength selector 430 acts as a filter to prevent radiation that is not within a predetermined range from being input into detector 418. This filter may be a tunable filter to allow sweeping of a predetermined band width and/or tracking of a tunable coherent source. Additionally, detector 414 may be coupled to the output of input coupler 412. The output of detector 414 is provided to processor 420 via signal line 422 for use in determining when resonant fiber optic ring 402 has received sufficient radiation by which to perform SPR analysis.

Figure 7D:
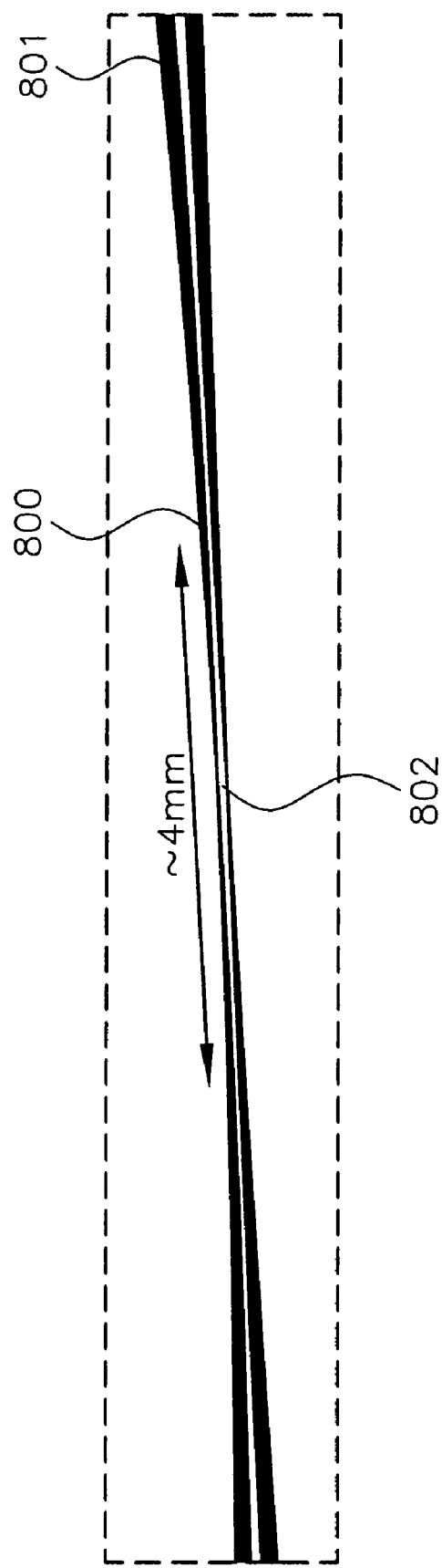
FIG. 7D is a top plan drawing illustrating features of an exemplary tapered fiber portion that may be used in the exemplary SPR sensor illustrated in FIG. 7A.
Figure 8A:
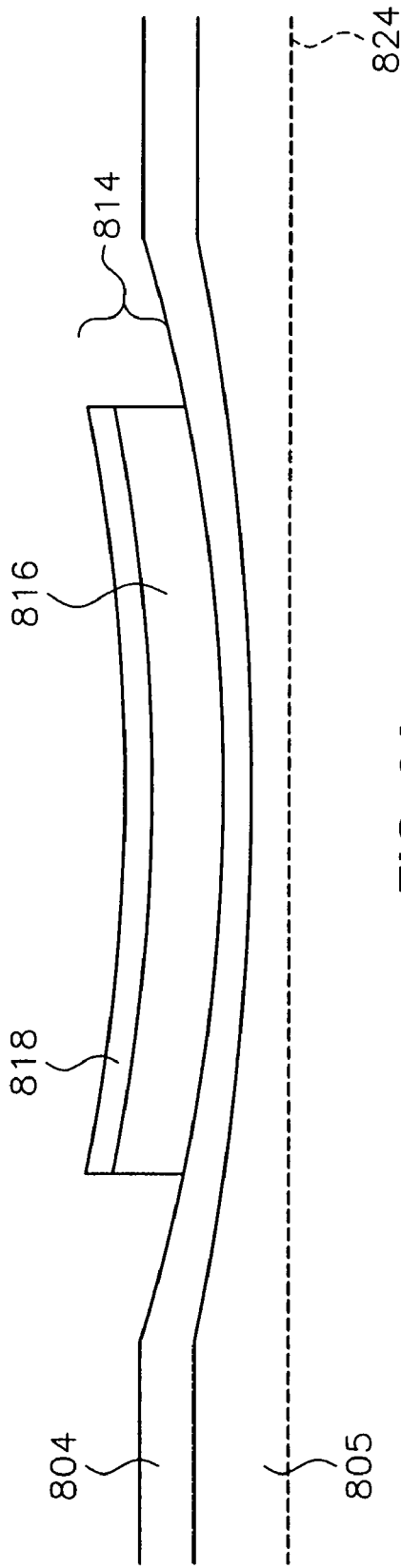
FIG. 8A a side cut-away drawing illustrating an exemplary SPR layer that may be included in the exemplary SPR sensors illustrated in FIGS. 7A, 9A, and 10A.

FIGS. 7A-D illustrate an exemplary SPR sensor that may be used in the exemplary SPCRD system of the present invention such as the exemplary system of FIG. 4. As shown in FIGS. 7A and 7D, sensor 800 is formed from fiber 801 by tapering the inner core 804 and cladding 805 to create tapered region 802 having tapered inner core 808 and tapered cladding 809. The forming of tapered region 802 may be accomplished using either of two techniques. The first technique is heating of a localized section of fiber 801 and simultaneous adiabatic pulling on either side of the region in which it is desired to form sensor 800. This procedure creates a constant taper in fiber 801. SPR layer 814 is then formed over at least a portion of the surface of tapered region 802.

Figure 8B:
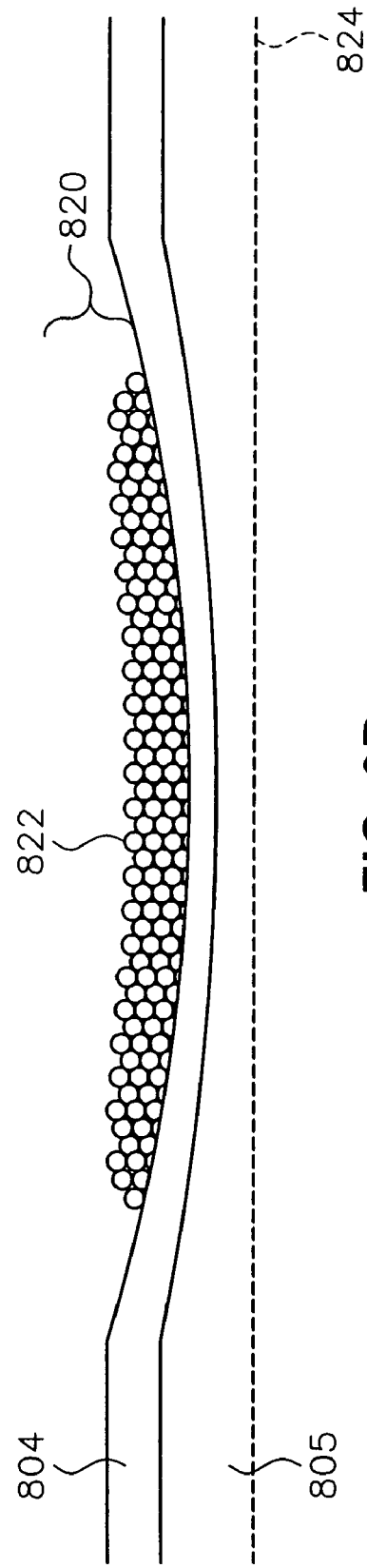
FIG. 8B a side cut-away drawing illustrating an alternative exemplary SPR layer that may be included in the exemplary SPR sensors illustrated in FIGS. 7A, 9A, and 10A.

FIGS. 8A and 8B show the upper half of an exemplary SPR sensor according to the present invention, illustrating exemplary SPR layers. Dashed lines 824 in FIGS. 8A and 8B indicate the axes of the optical fibers used in these exemplary SPR sensors. As shown in FIG. 8A, SPR layer 814 includes thin, conductive layer 816 on which the surface plasmons are generated. This layer may be formed by standard deposition techniques, such as sputtering, vaporization, or epitaxy, or it may be sprayed or painted onto the tapered fiber. Conductive layer 816 includes a conductive material such as a metal or conductive polymer, for example.

FIG. 8A also shows functionalized chemical coating 818, which may be formed on conductive layer 816. Functionalized chemical coating 818 may be formed of numerous materials, depending on the environmental changes to be measured. An example of one such coating material that may be used to concentrate analytes is polyethylene. Additionally, antigen specific binders may be used to attract a desired biological analyte with high specificity. The desired method of forming this coating may vary depending on the material of which it is formed.

Additionally, functionalized chemical coating 818 may be formed in a number of sections on conductive layer 816, which may be arranged in a desired pattern, such as strips along the length of the sensor or bands around the circumference. These sections may be formed of different materials to allow sensing of multiple environmental changes (or multiple analytes) with a single SPR sensor. The multiple coating sections may be designed to respond to a single wavelength of radiation providing a single alert to any one of the sensed changes (or analytes), or they may be designed to respond different wavelengths provides multi-channel sensing capabilities.

As described above, the inventors have discovered that the advantages provided by utilizing both SPR and CRDS are applicable to measuring environmental changes in the vicinity of the SPR sensor. These environmental changes may directly affect the index of refraction of the fluid surrounding the SPR sensor or may be assisted by functionalized chemical coating 818 formed as part of SPR layer 814. The functionalized chemical used in this coating may change its index of refraction based on a number of environmental changes, including: temperature; humidity; pH; electric field; and ionizing radiation. The functionalized chemical coating may also respond to binding events on its surface allowing an exemplary SPCRD system to detect the presence of minute quantities of specific chemical and biological agents. Conventional use of CRDS alone has the disadvantage that the sensitivity of a tapered optical fiber resonator without SPR is limited by to absorption by analytes exposed to enhanced evanescent field 810 in the tapered sensing region 812.

One issue with the use of SPR sensor is the wavelength range of operation. Typical metal conductive layers are capable of supporting surface plasmons generated by radiation with wavelengths in the range of 500 nm-600 nm. Although, there are many different types of optical fiber currently available, it may be desirable to be able to use one of the relatively inexpensive, low loss fibers developed for telecommunications applications in an exemplary SPR sensor of the present invention. One example is Corning's SMF-28e fused silica fiber which has achieved standard use in telecommunications applications. Specialty fibers exist that transmit light at a multitude of different wavelengths, such as a 488 nm/514 nm single mode fiber, manufactured by 3M of Austin, Tex. (part no. FS-VS-2614), 630 nm visible wavelength single-mode fiber manufactured by 3M of Austin, Tex. (part no. FS-SN-3224), 820 nm standard single-mode fiber manufactured by 3M of Austin, Tex. (part no. FS-SN-4224), and 0.28-NA fluoride glass fiber with 4-micron transmission, manufactured by KDD Fiberlabs of Japan (part no. GF-F-160). Further, and as mentioned above, fiber optic cable 402 may be a hollow fiber.

The wavelength of light affects optical mode conversion within the tapered region and therefore sensitivity, but this effect can be balanced by the taper design. For highest sensitivity, the wavelength should preferably be chosen to match the design wavelength of the fiber. Although some wavelengths may be more sensitive to mode conversion, it is anticipated that wavelengths far from the fiber's design wavelength will erode the desired sensitivity by causing too much transmission loss and an unusable ring-down signal. In one exemplary embodiment, the wavelength is 1550 nm (the minimum loss wavelength in telecom fiber), for which most inexpensive, durable telecommunications components are optimized. Other wavelengths are also suitable, however, such as 1300 nm (the zero dispersion wavelength in telecom fiber), although it is contemplated that the present invention may be used with wavelengths in the range of between 1250 nm and 1650 nm.

Alternatively, it may be desirable to use light with wavelengths in the range of 400 nm to 700 nm. Although the absorption of such light by standard optical fibers may be undesirably high, the light in this wavelength range may have an advantage for exciting surface plasmons. Thus, improvements in low loss visible band optical fibers may allow for the design of an improved SPCRD system.

FIG. 8B illustrates an alternative exemplary SPR layer 820 that may be used to extend the wavelength range of metal film based SPR sensors. Alternative SPR layer 820 is formed of numerous metal coated dielectric nano-particles 822. These metal coated dielectric nano-particles have a diameter of less that about 1 µm, desirably in the range of 5 nm-25 nm. The wavelength range of radiation for which alternative SPR layer 820 supports surface plasmons may be affected by both the diameter of metal coated dielectric nano-particles 822 and the dielectric properties of the dielectric material from which the nano-particles are formed. Metal coated dielectric nano-particles 822 may also be coated with a functionalized chemical coating. It is noted that nano-particles having different functionalized chemical coatings may be combined in a single SPR layer to form a multi-channel SPR sensor, similar to the multiple coating sections described with regard to FIG. 8A above. Metal coated dielectric nano-particles 822 may be adhered electrostatically to the optical fiber, as shown in FIG. 8B, or may be held in a polymer matrix (not shown). If metal coated dielectric nano-particles 822 are held in a polymer matrix, then the polymer matrix may desirably function as a functionalized chemical coating for the exemplary SPR sensor.

FIG. 7B illustrates a cross section of sensor 800 in the pre taper and post taper regions. As shown in FIG. 7B, inner core 804 and cladding 805 are in an unmodified state. It should be noted, for simplicity, the illustrations and description do not refer to the jacketing of fiber optic cable 801, though such jacketing is assumed to be in place for at least a portion of fiber optic cable 801.

FIG. 7C, illustrates a cross section of sensor 800 in tapered region 802. As shown in FIG. 7C, tapered inner core 808 and tapered cladding 809 each have a significantly reduced diameter as compared to inner core 804 and cladding 805 and have been covered by SPR layer 814. Tapered region 802 may be of any desired length based on the particular application. In the exemplary embodiment, as shown in FIG. 7D, for example, the length of the tapered region is approximately 4 mm with a waist diameter of about 12 microns.

Referring again to FIG. 7A, evanescent field 806 in the region of inner core 804 is narrow and confined when compared to enhanced evanescent field 810 in tapered region 802. As illustrated, enhanced evanescent field 810 is easily exposed to SPR layer 814 to allow generation of surface plasmons as discussed above with respect to the earlier exemplary embodiments and, thus, is better able to detect the desired environmental changes.

Figure 9A:
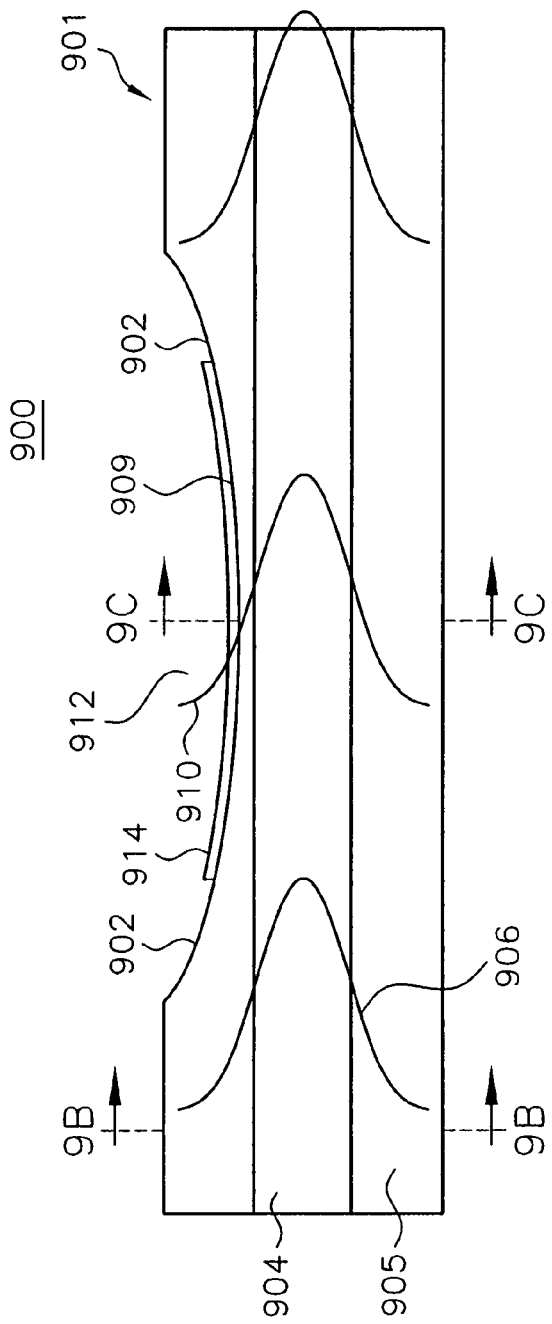
Figure 9C:
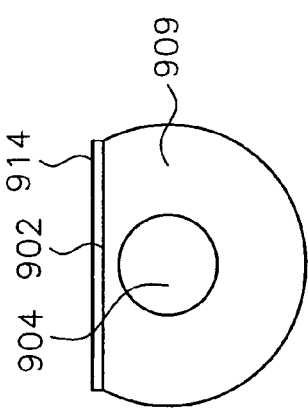
FIGS. 9B and 9C are end cut-away drawings illustrating features of the exemplary SPR sensor illustrated in FIG. 9A.
Figure 9B:
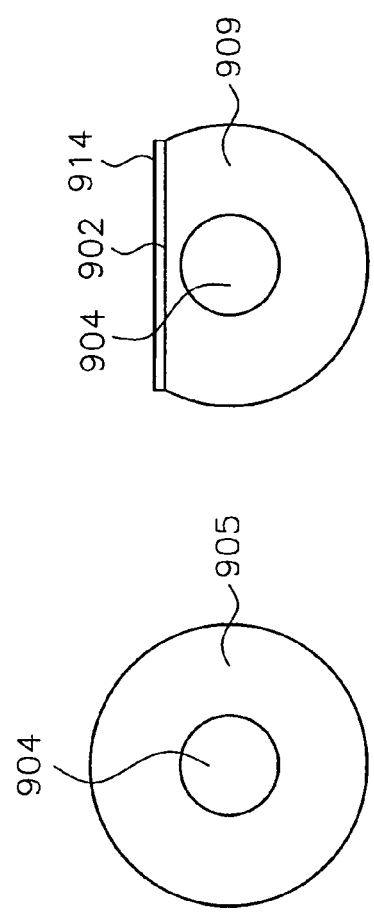

FIGS. 9A-9C illustrate another exemplary SPR sensor 900 that may be used to detect environmental changes. As shown in FIG. 9A, sensor 900 is formed from fiber 901 by removing a portion of cladding 905 to create a substantially "D" shaped cross section region 902. The forming of "D" shaped cross section region 902 may be accomplished by polishing one side of optical fiber cladding 905 using an abrasive, for example. The abrasive is used to remove cladding 905 in continuously increasing depths along region 902 to preserve guided mode quality, ultimately reaching a maximum depth at the point of minimum thickness of cladding 909. SPR layer 914 is then formed over at least a portion of the surface of tapered region 902. This area of lowest cladding thickness represents the region of maximum evanescent exposure 910.

FIGS. 10A-10C illustrate a further exemplary SPR sensor 1000 used that may be used to detect environmental changes. SPR sensor 1000 is formed using the second technique described above with respect to the tapered sensor exemplary embodiment. As shown in FIG. 10A, SPR sensor 1000 is formed from fiber 1001 by removing a portion of cladding 1005 using a chemical agent, known to those of skill in the art, to create tapered region 1002 having tapered cladding 1009. It is important that the chemical agent not be permitted to disturb or remove any portion of the inner core, as this may introduce significant losses in SPR sensor 1000. SPR layer 1014 is then formed over at least a portion of the surface of tapered region 1002.

FIG. 10B illustrates a cross section of SPR sensor 1000 in the pre taper and post taper regions. As shown in FIG. 10B, inner core 1004 and cladding 1005 are in an unmodified state. It should again be noted, for simplicity, the illustrations and description do not refer to the jacketing of fiber optic cable 1001, though such jacketing is assumed to be in place for at least a portion of fiber optic cable 1001.

FIG. 10C illustrates a cross section of SPR sensor 1000 in tapered region 1002. As shown in FIG. 10C, inner core 1004 is not affected while tapered cladding 1009 has a significantly reduced diameter as compared to cladding 1005 and SPR layer 1014 has been formed over tapered cladding 1009. Tapered region 1002 may be of any desired length based on the particular application. In the exemplary embodiment, for example, the length of the tapered region is approximately 4 mm with a waist diameter of about 12 microns.

Referring again to FIG. 10A, evanescent field 1006 in the region of inner core 1004 is narrow and confined when compared to enhanced evanescent field 1010 in tapered region 1002. As illustrated, enhanced evanescent field 1010 is easily exposed to SPR layer 814 to allow generation of surface plasmons as discussed above with respect to the earlier exemplary embodiments and, thus, is better able to detect the desired environmental changes.

With respect to the above described sensors 800, 900 and 1000, losses created in the optical fiber by forming the sensors may be balanced with the amount of evanescent field exposure to the SPR layer by determining the appropriate taper diameter or polish depth for the desired detection limits prior to fiber alteration. Further, it may be desirable to provide a protective mounting for sensors 800, 900 and/or 1000 to compensate for increased fragility due to the respective tapering and polishing operations.

It is contemplated that sensors 800, 900 and/or 1000 may be used in either as an unrestricted fiber, on a cylindrical core element (which may be solid, hollow or otherwise permeable), such as a mandrel or in a loop or bent configuration (not shown), as described in U.S. patent application Ser. No. 10/017,367 filed Dec. 12, 2001.

Figure 12:
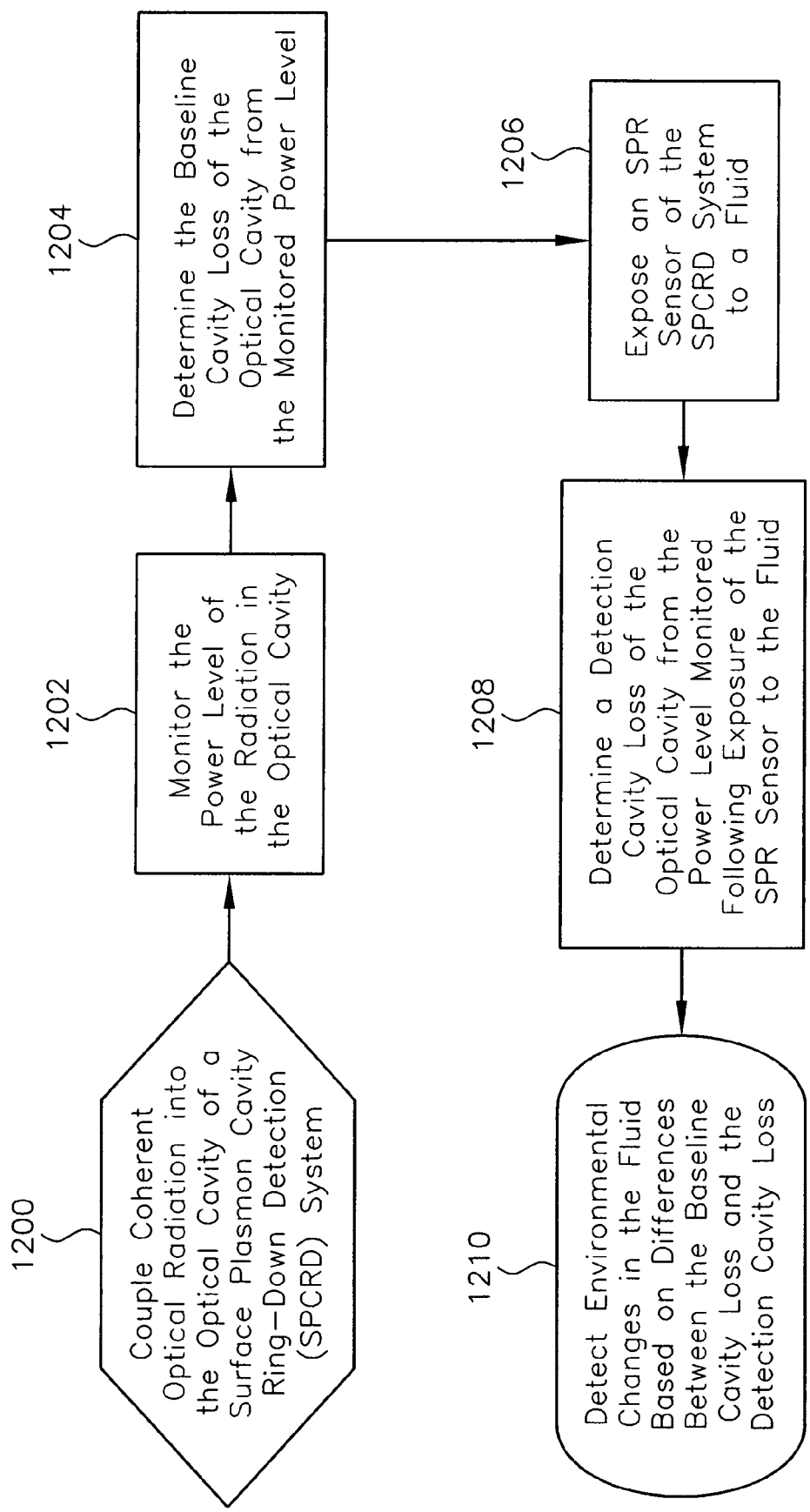
FIG. 12 is a flowchart illustrating an exemplary method for using an SPCRD system to detect environmental changes according to an exemplary embodiment of the present invention.

FIG. 12 is a flowchart illustrating an exemplary method of using an exemplary SPCRD system according to the present invention to detect environmental changes in a fluid. Coherent optical radiation is coupled into the optical cavity of the SPCRD system, step 1200. The coherent optical radiation may be either pulsed or CW. This coherent optical radiation desirably includes a predetermined wavelength.

The power level of the coherent optical radiation in the optical cavity is monitored, step 1202, and a baseline cavity loss of the optical cavity is determined based on the monitored power level, step 1204. The baseline cavity loss may be determined based on the average monitored power level of the coherent optical radiation in the optical cavity, if the coherent optical radiation being coupled into the cavity is CW. This average monitored power level represents an equilibrium between the coherent optical radiation being coupled into the cavity and the cavity losses. If the coherent optical radiation being coupled into the cavity is pulsed, however, the baseline cavity loss is determined based on a rate of decay of the monitored power level of the coherent optical radiation in the optical cavity. A mechanical chopper may be used to pulse a CW source.

It is noted that detection of the decay rate is preferred over detection of the cavity equilibrium power level due to the increased sensitivity of this method. The decay rate involves only the behavior of radiation already in the optical cavity at the start of the measurement and is, therefore, less sensitive to noise in the coherent source.

The SPR sensor of the SPCRD system is then exposed to the fluid to be monitored for environmental changes, step 1206, and a detection cavity loss of the optical cavity based on the monitored power level following exposure of the SPR sensor to the fluid, step 1208. The detection cavity loss in step 1208 is determined in the same manner as the baseline cavity loss in step 1204, depending on whether the coherent optical radiation being coupled into the cavity is CW or pulsed.

Any environmental changes in the fluid are then detected based on differences between the baseline cavity loss and the detection cavity loss of the optical cavity, step 1210. It is noted that the fluid may have a different refractive index than the environment used to establish the baseline cavity loss value. If no functionalized chemical coating is used on the SPR sensor, this difference in refractive index is detected as the environmental change.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. An apparatus for use with a coherent optical source to detect environmental changes, the apparatus comprising:
    an optical cavity, comprising an input coupling port, and an optical fiber section, the optical fiber section comprises a detection portion coated with a conductive layer capable of supporting a surface plasmon to provide cavity loss, the surface plasmon responsive to the environmental changes adjacent the detection portion;
    the coherent optical source optically coupled to the input coupling port of the optical cavity to provide radiation to the optical cavity;
    a detector optically coupled to the optical cavity to monitor the radiation in the optical cavity; and
    a processor electrically coupled to the detector for analyzing the environmental changes adjacent the detection portion of the optical cavity based on a rate of decay of the radiation in the optical cavity monitored by the detector.

2. The apparatus according to claim 1, wherein:
    the optical cavity is a standing wave cavity tuned to a peak wavelength of the coherent optical source; and
    a standing wave pattern formed in the standing wave cavity by radiation from the coherent optical source comprises a plurality of antinodes.

3. The apparatus according to claim 2, wherein:
    the detector is optically coupled to at least one antinode of the standing wave pattern; and
    the detection portion of the optical fiber section comprises at least one antinode of the standing wave pattern.

4. The apparatus according to claim 3, further comprising an output coupling port adjacent the at least one antinode optically coupled to the detector.

5. The apparatus according to claim 1, wherein the optical cavity is a traveling wave cavity.

6. The apparatus according to claim 5, wherein the optical cavity is a closed fiber optic ring formed by the optical fiber section.

7. The apparatus according to claim 1 wherein the input coupling port of the optical cavity is one of:
    a grating coupler;
    a high reflectivity mirror; or
    an evanescent fiber coupler.

8. The apparatus according to claim 1, wherein the optical fiber cavity further comprises at least one other optical fiber section, each optical fiber section comprising at least one detection portion.

9. The apparatus according to claim 1 wherein the detection portion of the optical fiber section is a tapered fiber portion.

10. The apparatus according to claim 9 wherein the tapered fiber portion is formed by heating and adiabatic stretching of the optical fiber section.

11. The apparatus according to claim 1 wherein the optical fiber section further comprises at least one other detection portion.

12. The apparatus according to claim 1 wherein the conductive layer coating the detection portion of the optical fiber section comprises a metal film formed on the detection portion of the optical fiber section.

13. The apparatus according to claim 1, wherein the conductive layer coating the detection portion of the optical fiber section comprises a plurality of metal coated dielectric nano-particles, each dielectric nano-particle having a diameter less than about 1 µm.

14. The apparatus according to claim 1, wherein:
    the detection portion of the optical fiber section further comprises a functionalized chemical coating over the conductive layer coating; and
    a refractive index of the functionalized chemical coating is responsive to the environmental changes adjacent the detection portion.

15. The apparatus according to claim 14 wherein the functionalized chemical coating is adapted to concentrate a predetermined analyte.

16. The apparatus according to claim 14 wherein the functionalized chemical coating comprises a plurality of chemical coating sections, each chemical coating section adapted to concentrate a different predetermined analyte.

17. The apparatus according to claim 14, wherein the environmental changes to which a refractive index of the functionalized chemical coating is responsive comprise at least one of:
    a chemical composition of a fluid adjacent the detection portion;
    an ambient temperature adjacent the detection portion;
    humidity adjacent the detection portion;
    a pH adjacent the detection portion;
    an electric field adjacent the detection portion; and
    ionizing radiation adjacent the detection portion.

18. The apparatus according to claim 1 wherein the environmental changes to which the surface plasmon is responsive comprise a refractive index of material in contact with the conductive layer.

19. The apparatus according to claim 1 wherein the optical fiber section is formed from at least one of plastic, fused silica, sapphire, or fluoride based glass.

20. The apparatus according to claim 1, wherein the optical fiber section is formed from a hollow optical fiber.

21. The apparatus according to claim 1, wherein the optical fiber section is one of a single mode optical fiber or a multi-mode optical fiber.

22. The apparatus according to claim 1 wherein the optical fiber section resonates at a wavelength between a visible region of an electro-magnetic spectrum and a mid-infrared region of the electro-magnetic spectrum.

23. The apparatus according to claim 1, wherein the optical fiber section is at least about 1 m long.

24. The apparatus according to claim 1, wherein the optical fiber section is at least about 10 m long.

25. The apparatus according to claim 1, wherein the optical fiber section is at least about 1 km long.

26. The apparatus according to claim 1 wherein the coherent optical source comprises at least one of an optical parametric generator or an optical parametric amplifier.

27. The apparatus according to claim 1 wherein the coherent optical source is a laser source.

28. The apparatus according to claim 27 wherein the laser source comprises one of a pulsed laser or a continuous wave laser.

29. The apparatus according to claim 27 wherein the laser source comprises one of an optical fiber laser or a tunable diode laser having a narrow band.

30. The apparatus according to claim 27, wherein the laser source is a single mode laser tunable in the wavelength region of about 400 nm and about 700 nm.

31. The apparatus according to claim 27 wherein the laser source is a single mode laser tunable in the wavelength region of about 1250 nm and about 1650 nm.

32. The apparatus according to claim 1, wherein the radiation provided to the optical cavity by the coherent optical source is single mode laser light having a predetermined peak wavelength.

33. The apparatus according to claim 32, wherein the predetermined peak wavelength is in a first range of about 400 nm to about 700 nm or a second range of about 1250 nm to about 1650 nm.

34. The apparatus according to claim 1, wherein:
the radiation provided to the optical cavity by the coherent optical source has a plurality of spectral peaks, each spectral peak having a corresponding peak wavelength;
the detector optically monitors each spectral peak of the radiation in the optical cavity separately; and
the processor analyzes the environmental changes adjacent the detection portion of the optical cavity based on a plurality of spectral peak rates of decay of corresponding to the plurality of spectral peak of the radiation in the optical cavity.

35. The apparatus according to claim 34, wherein the optical cavity comprises a plurality of detection portions, each detection portion having a corresponding conductive layer capable of supporting a corresponding surface plasmon to provide cavity loss at one corresponding peak wavelength.

36. The apparatus according to claim 35 wherein:
each detection portion of the optical fiber section further comprises a corresponding functionalized chemical coating;
each functionalized chemical coating is adapted to concentrate a corresponding predetermined analyte; and
a refractive index of each functionalized chemical coating is responsive to an amount of the corresponding predetermined analyte concentrated.

37. The apparatus according to claim 1, further comprising:
an optical isolator optically coupled between the coherent optical source and the input port of the optical cavity and in line with the radiation emitted from the coherent optical source such that the optical isolator minimizes noise from the coherent optical source.

38. The apparatus according to claim 1 wherein the detector is an inline electroabsorption monitor in the optical fiber section.

39. The apparatus according to claim 1 wherein:
the optical cavity further comprises an output port;
the output port comprises at least one of;
a grating coupler;
a high reflectivity mirror; or
an evanescent fiber coupler; and
the detector is optically coupled to the optical cavity through the output port.

40. The apparatus according to claim 39, wherein the detector comprises at least one of a photodiode, a photoresistor, or a phototransistor.

41. The apparatus according to claim 39 wherein the apparatus further comprises a filter placed in an optical path between the output port and the detector to selectively pass a portion of the radiation from the optical cavity to the detector.

42. The apparatus according to claim 41, wherein the filter is a tunable filter.

43. The apparatus according to claim 1 further comprising an input detector for determining when the radiation from the coherent optical source is provided to the optical cavity.

44. The apparatus according to claim 43 further comprising optical source control means to deactivate the coherent optical source after the input detector determines that the coherent optical source has provided the radiation to the optical cavity.

45. The apparatus according to claim 44, wherein the control means and the input detector are electrically coupled to the processing means.

46. The apparatus according to claim 43, wherein:
the input detector is electrically coupled to the processor and transmits a trigger signal to the processor when the radiation from the coherent optical source is provided to the optical cavity; and
the processor begins analyzing the rate of decay of the radiation in the optical cavity when the trigger is received from the input detector.

47. An apparatus to detect binding events for use with a coherent source that emits radiation, the apparatus comprising:
a passive, closed fiber optic ring;
a sensor having a predetermined shape, a conductive coating, and being in line with the passive, closed fiber optic ring, the conductive coating capable of supporting a surface plasmon driven by a propagating field in the passive, closed fiber optic ring and responsive to a level of the binding events at a surface of the conductive coating;

coupling means for i) optically coupling at least a portion of the radiation emitted by the coherent source into the passive, closed fiber optic ring to generate the propagating field in the passive, closed fiber optic ring and ii) transmitting a detection portion of the propagating field from the passive, closed fiber optic ring;
a detector for detecting a power level of the detection portion of the propagating field transmitted by the coupling means and generating a signal responsive thereto; and
a processor electrically coupled to the detector for determining the level of the binding events on the surface of the conductive coating of the sensor based on a rate of decay of the power level of the detection portion of the propagating field detected by the detector.

48. The apparatus according to claim 47, wherein:
the predetermined shape of the sensor is a tapered portion formed between ends of the sensor; and
the predetermined shape is exposed to a surrounding fluid.

49. The apparatus according to claim 48 wherein the tapered portion is formed by heating and adiabatic stretching of a sensor section of the passive, closed fiber optic ring.

50. The apparatus according to claim 48, wherein the fluid is at least one of a gas, a liquid, or a suspension.

51. The apparatus according to claim 47 wherein the conductive coating of the sensor is excitable when a wavelength of the propagating field in the passive, closed fiber optic ring matches a characteristic plasmon resonance wavelength of the conductive coating.

52. The apparatus according to claim 51 wherein the sensor further comprises a functionalized chemical coating formed on the conductive coating.

53. The apparatus of claim 52, wherein the functionalized chemical coating is adapted to concentrate a predetermined analyte.

54. The apparatus according to claim 47, wherein the conductive coating of the sensor comprises a metal film.

55. The apparatus according to claim 47, wherein the conductive coating of the sensor comprises a plurality of metal coated dielectric nano-particles, each dielectric nano-particle having a diameter less than about 1 μm.

56. The apparatus according to claim 47 wherein the coupling means is a single optical coupler.

57. The apparatus according to claim 47, wherein the coupling means comprises i) a first optical coupler for optically coupling the portion of the radiation emitted by the coherent source into a first section of the passive, closed fiber optic ring and ii) a second optical coupler for transmitting the detection portion of the propagating field from a second section of the passive, closed fiber optic ring.

58. The apparatus according to claim 47 further comprising a filter placed in an optical path between the coupling means and the detector to selectively pass the detection portion of the propagating field transmitted by the coupling means from the passive, closed fiber optic ring to the detector.

59. The apparatus according to claim 58 wherein the filter selectively passes the detection portion of the propagating field to the detector based on a wavelength of the detection portion.

60. The apparatus according to claim 47 wherein the coherent source comprises at least one of:
an optical parametric generator;
an optical parametric amplifier; or
a laser source.

61. The apparatus according to claim 47 further comprising:
an optical isolator coupled between the coherent source and the coupling means and in line with the radiation emitted by the coherent source such that the optical isolator minimizes noise reflected back into the coherent source.

62. The apparatus according to claim 47, wherein the surface plasmon generated on the surface of the conductive coating of the sensor dissipates the propagating field in the passive, closed fiber optic ring.

63. The apparatus according to claim 47, wherein the passive, closed fiber optic ring is formed from at least one of plastic, fused silica, sapphire, or fluoride based glass.

64. The apparatus according to claim 47, wherein the passive, closed fiber optic ring is formed from a hollow optical fiber.

65. The apparatus according to claim 47 wherein the passive, closed fiber optic ring is formed from one of a single mode optical fiber or a multi-mode optical fiber.

66. The apparatus according to claim 47 wherein a coupled power of the input portion of the radiation coupled into the passive, closed fiber optic ring is less than about 1% of an emitted power the radiation emitted by the coherent source.

67. The apparatus according to claim 47 wherein a coupled power of the input portion of the radiation coupled into the passive, closed fiber optic ring is variable.

68. The apparatus according to claim 67, wherein:
the coupled power of the input portion of the radiation is varied based on a loop loss within the passive, closed fiber optic ring; and
the loop loss is based on at least connector losses and fiber losses.

69. The apparatus according to claim 67 wherein a circumference of the passive, closed fiber optic ring is at least about 1 m.

70. The apparatus according to claim 67, wherein a circumference of the passive, closed fiber optic ring is at least about 10 m.

71. The apparatus according to claim 67 wherein a circumference of the passive, closed fiber optic ring is at least about 1 km.

72. An improved method of detecting environmental changes in a fluid using a surface plasmon cavity ring-down detection (SPCRD) system that comprises a surface plasmon resonance (SPR) sensor optically coupled within an optical cavity, the SPR sensor formed of a metal-coated tapered optical fiber section, the method comprising:
coupling coherent optical radiation into the optical cavity of the SPCRD system, the coherent optical radiation comprising a predetermined wavelength;
monitoring a power level of the coherent optical radiation in the optical cavity;
determining a baseline cavity loss of the optical cavity based on the monitored power level;
exposing the SPR sensor to the fluid;
determining a detection cavity loss of the optical cavity based on the monitored power level following exposure of the SPR sensor to the fluid; and
detecting environmental changes in the fluid based on differences between the baseline cavity loss and the detection cavity loss of the optical cavity.

73. The method according to claim 72, wherein:
the coherent optical radiation coupled into the optical cavity is constant wave optical radiation;

the baseline cavity loss is determined based on an average monitored power level of the coherent optical radiation in the optical cavity monitored before exposure of the SPR sensor to the fluid; and the detection cavity loss is determined based on the average monitored power level of the coherent optical radiation in the optical cavity monitored after exposure of the SPR sensor to the fluid.

74. The method according to claim 72 wherein:

the coherent optical radiation coupling into the optical cavity is pulsed optical radiation;

the baseline cavity loss is determined) based on a rate of decay of the monitored power level of the coherent optical radiation in the optical cavity monitored before exposure of the SPR sensor to the fluid; and the detection cavity loss is determined based on the rate of decay of the monitored power level of the coherent optical radiation in the optical cavity monitored after exposure of the SPR sensor to the fluid.

\* \* \* \* \*

UNITED STATES PATENT AND TRADEMARK OFFICE
CERTIFICATE OF CORRECTION

PATENT NO. : 7,352,468 B2 Page 1 of 1
APPLICATION NO. : 11/021572
DATED : April 1, 2008
INVENTOR(S) : Peter B. Tarsa It is certified that error appears in the above-identified patent and that said Letters Patent is hereby corrected as shown below:

At Column 1, line 12, insert:

GOVERNMENT FUNDING

This invention was made with Government support under National Science Foundation Grant No. CHE-0228797. The Government has certain rights in the invention.

Signed and Sealed this

Twenty-ninth Day of July, 2008

JON W. DUDAS
*Director of the United States Patent and Trademark Office*